US012606459B2

(12) United States Patent
Klein et al.

(10) Patent No.: US 12,606,459 B2
(45) Date of Patent: Apr. 21, 2026

(54) BATCH POLYFLUOROALKYL SUBSTANCES (PFAS) PILOT METHODS, MOBILE APPARATUS, AND ROUGHING FILTER SYSTEM AND METHODS

(71) Applicant: Sentinel Water Solutions, LLC, State College, PA (US)

(72) Inventors: Thomas E Klein, West Chester, PA (US); Andrew L Strassner, Malvern, PA (US)

(73) Assignee: Sentinel Water Solutions, LLC, State College, PA (US)

( * ) Notice: Subject to any disclaimer, the term of this patent is extended or adjusted under 35 U.S.C. 154(b) by 0 days.

(21) Appl. No.: 19/403,113

(22) Filed: Nov. 27, 2025

(65) Prior Publication Data

US 2026/0091988 A1     Apr. 2, 2026

Related U.S. Application Data

(63) Continuation of application No. PCT/US2025/030135, filed on May 20, 2025.
(Continued)

(51) Int. Cl.
*C02F 1/28*          (2023.01)
*B09C 1/00*          (2006.01)
(Continued)

(52) U.S. Cl.
CPC .............. *C02F 1/008* (2013.01); *C02F 1/283* (2013.01); *C02F 1/42* (2013.01); *G01N 1/4005* (2013.01);
(Continued)

(58) Field of Classification Search
CPC .... B09C 1/00; C02F 1/008; C02F 1/28; C02F 2101/36; C02F 2209/001
See application file for complete search history.

(56) References Cited

U.S. PATENT DOCUMENTS 7,281,410 B2     10/2007   Phillips
8,361,920 B2      1/2013   Dong
(Continued)

OTHER PUBLICATIONS

Intuitech—"Water Treatment Pilot Plants", https://www.intuitech.com/, Apr. 29, 2025.
(Continued)

*Primary Examiner* — Dirk R Bass
(74) *Attorney, Agent, or Firm* — Bonini IP Law, LLC; Frank J. Bonini, Jr.

(57) ABSTRACT

Methods and apparatus for filtering contaminants from a water source, and for evaluating the effectiveness of filter media for a water source, involving flowing water from the water source into a filter media within a pressure vessel, generating an amount of filter media for filtering contaminants from the water source from contaminant concentrations of a plurality of samples of the water source obtained after contact with the filter media at different filter bed volumes and/or at different media heights within the sample filter vessel, from a generated forecast of the breakthrough point for the filter media. An apparatus comprising an array of pressure vessels with sampling features that comprises a mobile array for collecting the water samples from the water source after entry into a pressure vessel. A roughing filter system may be used separately or in conjunction with the filter media evaluation methods and apparatus.

23 Claims, 25 Drawing Sheets

Related U.S. Application Data

(60) Provisional application No. 63/649,502, filed on May 20, 2024.

(51) Int. Cl.

| | |
|---|---|
| *C02F 1/00* | (2023.01) |
| *C02F 1/42* | (2023.01) |
| *C02F 1/44* | (2023.01) |
| *G01N 1/40* | (2006.01) |
| *G01N 33/18* | (2006.01) |
| *C02F 101/36* | (2006.01) |

(52) U.S. Cl.
CPC .......... *G01N 33/18* (2013.01); *C02F 2101/36* (2013.01); *C02F 2201/005* (2013.01); *C02F 2201/008* (2013.01); *C02F 2301/08* (2013.01); *G01N 2001/4011* (2013.01)

(56) References Cited

U.S. PATENT DOCUMENTS

| | | |
|---|---|---|
| 10,590,019 B2 | 3/2020 | Ertel et al. |
| 2017/0209834 A1 | 7/2017 | Cohen et al. |
| 2018/0273400 A1 | 9/2018 | Schonfeld et al. |
| 2020/0147550 A1 | 5/2020 | Gefroh et al. |
| 2021/0002160 A1 | 1/2021 | Van Gils et al. |
| 2021/0300789 A1 | 9/2021 | Philips |
| 2022/0073375 A1 | 3/2022 | Smitty et al. |

OTHER PUBLICATIONS

"Treating PFOA and PFOS at the Hatboro Wells—GFT", Apr. 2025, https://www.gftinc.com/project/treating-pfoa-and-pfos-at-the-hatboro-wells/.

"Drinking Water Treatment for PFAS Selection Guide, Technical Support on Per- and Polyfluoroalkyl Substances Policy", American Water Works Association, (c) 2020.

Containerized / Mobile Water Treatment Equipment—Pure Aqua, Inc., 2015, https://pureaqua.com/containerized-water-treatment-equipment/.

GAC Filtration Trailer, https://acmeboom.com/gac-filtration-trailer, © 2024 ACME Environmental.

Mobile Horizontal Filter Trailer, https://www.evoqua.com/en/evoqua/products--services/services/short-term-operating-contract/mobile-horizontal-fi lter-trailer/.

H.C. Croll et al., "Fundamental kinetic constants for breakthrough of per- and polyfluoroalkyl substances at varying empty bed contact times: Theoretical analysis and pilot scale demonstration", Chemical Engineering Journal 464 (2023) 142587, 1-13.

Per- and Polyfluoroalkyl Substances (PFAS), https://www.epa.gov/sdwa/and-polyfluoroalkyl-substances-pfas.

Final Progress Update, Emerging Contaminants Treatment Strategy Pilot Study, Nov. 1, 2017, Black & Veatch.

Calgon Carbon, Activated Carbon Equipment, 2019 Calgon Carbon Corporation.

Guide for Conducting Treatability Studies Under Cercla: Soil Vapor Extraction Interim Guidance, United States Environmental Protection Agency, EPA/540/2-91/019A, Sep. 1991.

Desotac, https://www.desotec.com/en-us?ppc_keyword=Desotec%20Red%20BI . . . ame&utm_term=Desotec%20Red%20Bluff&utm_content=Brand%20Name.

Kempisty, David et al., The Treatment of PFAS-Impacted Groundwater Using Novel Regenerable Ion Exchange Resin: A Five-Year Case Study, Australian Water Journal, vol. 10 No. 3 2024.

Woodard, Steven et al., "Ion Exchange resin for PFAS removal and pilot test comparison to GAC", Remediation Journal: vol. 27, Issue 3, Jun. 7, 2017.

Chart Water, Exclusive Distributor for PFAS Guard LLC, Copyright 2025.

"Per- and Polyfluoroalkyl Substances", https://tdb.epa.gov/tdb/contaminant?id=11020.

Existing Process for Traditional Pilot and RSSCT

210 — START

211 — PREDETERMINED TIME REACHED Y/N?

212

NO

213 — YES

214 — COLLECT BATCH OF WATER SAMPLES

215 — CONVERT EACH DATA POINT TO "FULL SCALE" EQUIVALENT

216 — CREATE FORECAST FOR FULL- SCALE PERFORMANCE

END

SAMPLE DATA ANALYSIS FOR TRADITIONAL/RSSCT PILOT MEDIA LIFE

*FIG. 6*

BATCH SAMPLE DATA ANALYSIS FOR FORECASTED PILOT MEDIA LIFE

FORECASTED BREAKTHROUGH

PFAS THRESHOLD (VARIES BY CONTAMINANT)

DATA COLLECTED FROM BATCH OF SAMPLES FOR FIXED PILOT DURATION / BED VOLUMES

FORECASTED BED VOLUMES

PFAS Concentration [ppt]

Depth [in]

BATCH POLYFLUOROALKYL SUBSTANCES (PFAS) PILOT METHODS, MOBILE APPARATUS, AND ROUGHING FILTER SYSTEM AND METHODS

BACKGROUND OF THE INVENTION

1. Field of the Invention

The present invention applies to the field of water and wastewater treatment pilot processes, and more particularly to methods and apparatus for sampling and monitoring substances in water and wastewater, including contaminants and potential contaminants, and other substances, and to devices and methods for treatment of water and wastewater.

2. Brief Description of the Related Art

Water and wastewater are typically monitored for substances which may be potential pollutants toxins or other harmful substances. A category of pollutants are polyfluoroalkyl substances commonly referred to as "PFAS". The PFAS are commonly referred to as "forever chemicals", and also within the group of PFAS are perfluorooctanesulfonic acid (PFOS) and perfluorooctanoic acid (PFOA). PFAS are widely used, long lasting chemicals, components of which break down very slowly over time. Because of their widespread usage, PFAS work their way into the water systems and other ecosystems. PFAS widespread use and persistence in the environment has resulted in many individuals and animals having PFAS in their blood. This is not limited to one geographic area, but is common worldwide. PFAS also are present at low levels in a variety of food products and in the environment, including for example in water, air, fish, and soil at locations worldwide. A number of studies have linked environmental PFAS to negative health effects in humans and other animals. The numbers of PFAS chemicals are vast, as there are thousands of PFAS chemicals which are widely used and can be found in a variety of consumer, household, commercial, and industrial products.

Therefore, water that serves as a source for drinking water and other uses must be monitored, as well as treated when potential contaminant levels are present or are determined to be at levels that are designated by some health, legal or other standard, to be a potential hazard. The Environmental Protection Agency (EPA) has set for a regulation establishing requirements for maximum allowable levels for six PFAS in drinking water. This regulation, entitled, National Primary Drinking Water Regulation (NPDWR) establishes legally enforceable levels, called Maximum Contaminant Levels (MCLs), for six PFAS and also sets forth non-enforceable Maximum Contaminant Level Goals (MCLGs) for the PFAS. The levels are set out in TABLE 1 below:

TABLE 1

| Compound | Final MCLG | Final MCL (enforceable levels) |
|---|---|---|
| PFOA | Zero | 4.0 parts per trillion (ppt) (also expressed as ng/L) |
| PFOS | Zero | 4.0 ppt |
| PFHxS | 10 ppt | 10 ppt |
| PFNA | 10 ppt | 10 ppt |
| HFPO-DA (commonly known as GenX Chemicals) | 10 ppt | 10 ppt |
| Mixtures containing two or | 1 (unitless) | 1 (unitless) |

TABLE 1-continued

| Compound | Final MCLG | Final MCL (enforceable levels) |
|---|---|---|
| more of PFHxS, PFNA, HFPO-DA, and PFBS | Hazard Index | Hazard Index |

There are presently only two main methods for PFAS pilot studies, one being the Traditional Pilot Testing (TPT), and the other the Rapid Small Scale Column Testing (RSSCT). In general, each method provide some utility, but each method also has a number of drawbacks. The pros and cons of each method is as follows:

Traditional Pilot Testing (TPT) has both benefits and drawbacks. TPT typically may provide more representative results, which include larger columns that better simulate the hydraulics, contact times, and operational conditions of a full-scale treatment system. These benefits have been reported to lead to more reliable performance data. McCleaf, P., Englehardt, J., Zilles, J., & Higgins, C. P. (2017). "Examination of per- and polyfluoroalkyl substance treatment using granular activated carbon pilot-scale columns. Water Research Institute Technical Report, 21". TPT may also provide operational insights, such as providing data on critical factors like backwashing frequency, potential fouling, pressure drop, and long-term media performance that RSSCTs cannot easily capture. (Id., McCleaf, P., et al.). In addition, TPT has gained regulatory acceptance, as it often is preferred by regulatory agencies due to the more comprehensive data it provides for full-scale system design. Despite these benefits, there are a number of drawbacks associated with TPT, which include higher costs, as TPT requires more media, larger equipment, and increased setup and operating expenses compared to RSSCTs. (Water Research Foundation. (2021). "Guidance for Conducting Treatability Studies for PFAS under CERCLA or RCRA".) In addition, TPT requires a longer duration, and can take weeks to months to complete, potentially delaying project timelines compared to faster RSSCTs. (Id., Water Research Foundation. (2021)). TPT also is less flexible and therefore TPT may not be ideal for rapid screening of a large number of potential treatment technologies or media options.

RSSCT (Rapid Small-Scale Column Test), like TPT has both benefits and drawbacks. RSSCT can be cost-effective, as it uses smaller media volumes and simplified equipment, reducing costs for initial screening investigations. (Water Research Foundation. (2021)). In addition, RSSCT Faster results: Can be completed in days to weeks, providing quicker insights into potential treatment options. C. Woodard, 2018. "Optimizing Ion Exchange and GAC for PFAS Removal. Water Quality Products." RSSCT also is suited for early screening by allowing to efficiently evaluate multiple media types or treatment technologies in parallel. However, despite some benefits, there are a number of drawbacks. RSSCT is typically less representative, and due to the smaller size, grinding of media, and shorter run times. RSSCTs may not fully reflect real-world treatment performance, especially with respect to long-term media behavior. (Id., C. Woodard, 2018) RSSCT also provides limited operational data, as it does not provide as much information on system hydraulics, pressure drop, or backwashing requirements. There are also scaling uncertainties with RSSCT. Extrapolating results from RSSCTs to full-scale systems often can introduce some uncertainty.

A need exists for a method and devices that can determine the presence and levels of contaminants, in particular PFAS, that can provide more rapid results with accuracy, without the drawbacks of the prior methods and devices.

SUMMARY OF THE INVENTION

The invention presents inventive methods and apparatus for PFAS pilot testing that are designed to improve the testing method and procedures for determining the presence and levels of PFAS. The methods of the invention retain the benefits of prior processes, but provide improvements by eliminating or minimizing the drawbacks of the prior testing methods, such as TPT and RSSCT. The inventive methods and apparatus are designed to facilitate and expedite results in a breakthrough determination for one or more filter media types. Embodiments of the invention also provide conservation of filter media by managing usage through arrangements coupled with optional monitoring to maximize utilization of the filter media capacity.

Specifically, the invention provides more cost-effective, flexible, and faster determinations than traditional pilot testing, and provides a greater number of representative results and better operational insight than prior methods, including the prior traditional method and the Rapid Small-Scale Column Test (RSSCT) method.

The present invention achieves the improved benefits by replacing the process by which traditional pilots tests and RSSCT are performed. In both traditional pilots tests and RSSCT, water is run through the test columns and grab samples are taken at regular time intervals by operators until breakthrough of the media occurs at the bottom of the column at an undetermined amount of elapsed time. Operating and sampling the pilot system is where significant pilot testing costs are incurred and time is consumed. Operating and sampling the pilot system also requires expertise which makes it difficult to scale and make widely available. The inventive methods and apparatus, according to some preferred embodiments and implementations, run water through a pilot apparatus for a predetermined amount of time. Once the predetermined amount of time has elapsed, a batch of samples from fixed depth intervals on each column is taken. The end of the test may be based on time, or the flow totalization. The next step involves the sample analysis, when the collected samples are analyzed. The sample analysis in the preferred embodiments and implementations involves batch forecasting analysis. According to preferred embodiments and implementations, the inventive method involves an analysis where samples are analyzed together to correlate concentration by depth, and breakthrough is forecasted. The batch process of the inventive methods and apparatus significantly reduces the costs incurred, time consumed, and expertise required to run the pilot which allows for the method and apparatus to be deployed at scale. Another benefit of the invention is that by reducing the costs and operating burden, it allows for the system to be run in parallel to a full-scale PFAS treatment system to predict breakthrough.

The invention also presents an alternative method for PFAS treatment at full scale that can be pilot tested or designed using various modeling techniques without a pilot study. The alternative method will be referred to throughout this document as a pressure vessel roughing filter (PVRF) for PFAS treatment, and its core advantage over traditional PFAS treatment methods using pressure vessels is an extended media life and more complete utilization of the media for the system. Those two main benefits translate to improved costs to operate the PFAS treatment system due to less frequent media changes which can often be logistically complicated and expensive operations. The pressure vessel roughing filter (PVRF) design applies to both GAC, ion exchange resins, and a variety of other media types including proprietary medias that are contained in pressure vessels.

When using a pilot study to design a PVRF system, the pilot study can be conducted using traditional pilot testing, RSSCT, or the pilot testing method of the invention. Although a variety of pilot testing methods can be employed, the benefits of using the pilot method disclosed in the invention are amplified significantly because of the extended media life from the PVRF system.

At a high level the pressure vessel roughing filter method works by placing more vessels in series than traditional treatment schemes and then ensuring that any vessels upstream of the final vessel of a treatment train are completely exhausted prior to media replacement.

BRIEF DESCRIPTION OF THE DRAWING FIGURES

FIG. 6 is a graph of a plot for sample analysis for traditional pilot (TPT) and RSSCT, showing bed volumes versus PFAS concentration.

DETAILED DESCRIPTION OF THE INVENTION

The inventive process and devices are utilized for evaluating and analyzing filtration media for effectiveness. Preferred embodiments of the invention are illustrated in exemplary implementations where a fluid, such as a water source, is tested. The method of taking a batch of samples after the expiration of a predetermined and fixed amount of time is applicable to a wide variety of apparatus. Below are four exemplary implementations of how to employ the method with an explanation of the associated apparatus. Preferred apparatus in accordance with the invention are depicted, but it should be noted that the embodiments described below for the invention include, but are not limited to the range of possible apparatus that can be employed to carry out and use the method of the invention.

Figure 1:
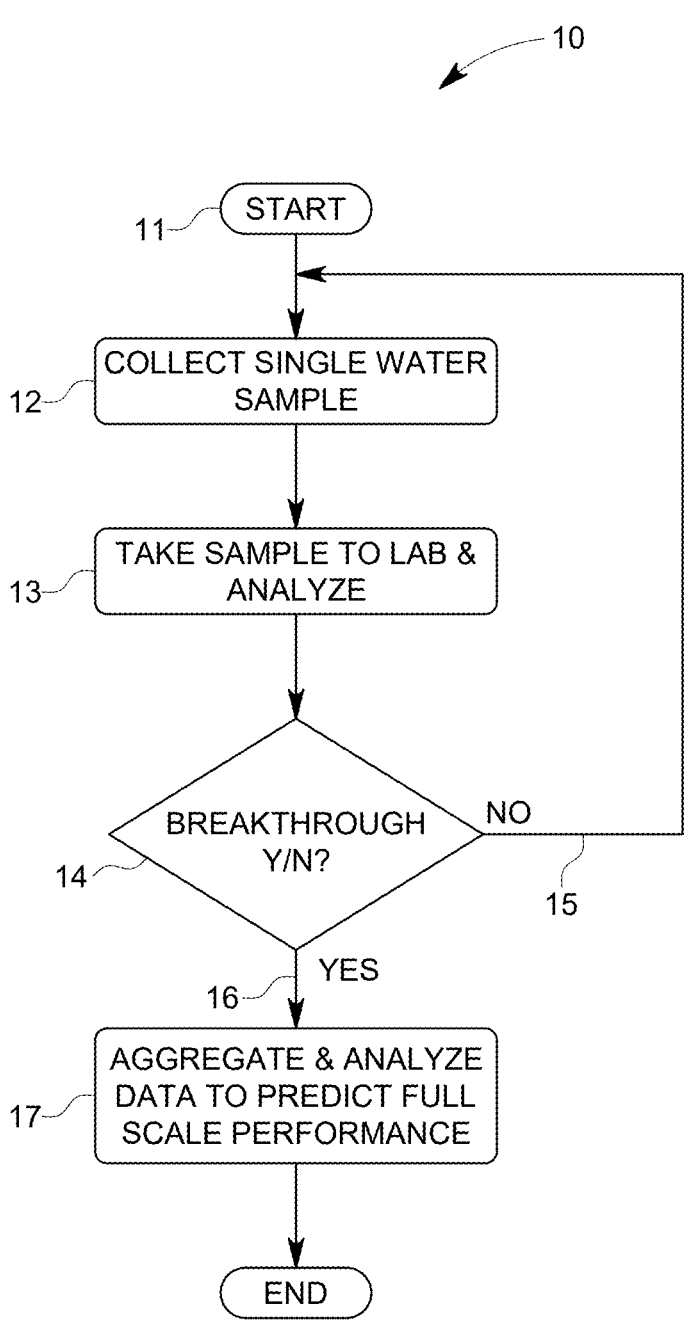
FIG. 1 is a flow diagram of an existing process for traditional pilot (TPT) and Rapid Small Scale Column Testing (RSSCT).

Referring to FIG. 1, there is illustrated a prior art existing process for traditional and RSSCT types of pilot tests where source water is run through a media column for any media being tested. Then samples are collected intermittently until breakthrough occurs. For traditional and RSSCT pilot tests, the time duration of the pilot until breakthrough occurs is indeterminate. Once breakthrough occurs the results of all samples collected intermittently are analyzed and correlated to anticipated full scale performance. FIG. 1 shows the prior process 10 where the start of the process commences with running the source water to be evaluated through the media for the media being tested, block 11, and then a water sample is collected, block 12. The sample is then taken from the collection location to a lab where the sample can be analyzed, block 13. The lab analysis determines whether there is a breakthrough, block 14. The breakthrough, block 14, determines next a first decision option where there is no breakthrough, decision path line 14, and a second decision option where the breakthrough has been determined to have occurred, decision line 15. When there has not been a determined breakthrough for the sample, path line 15, then the process continues, with the running of the source water to be evaluated through the media for the media being tested, block 11, and collecting a water sample, block 12, taking the sample to the lab, block 13, and determining whether there is a breakthrough, block 14, and if not, repeating these steps, until the determination is made that there is a breakthrough, decision path line, block 16. Once the breakthrough occurs, then the process aggregates and analyzes the data to predict the full-scale performance, block 17.

Figure 2:
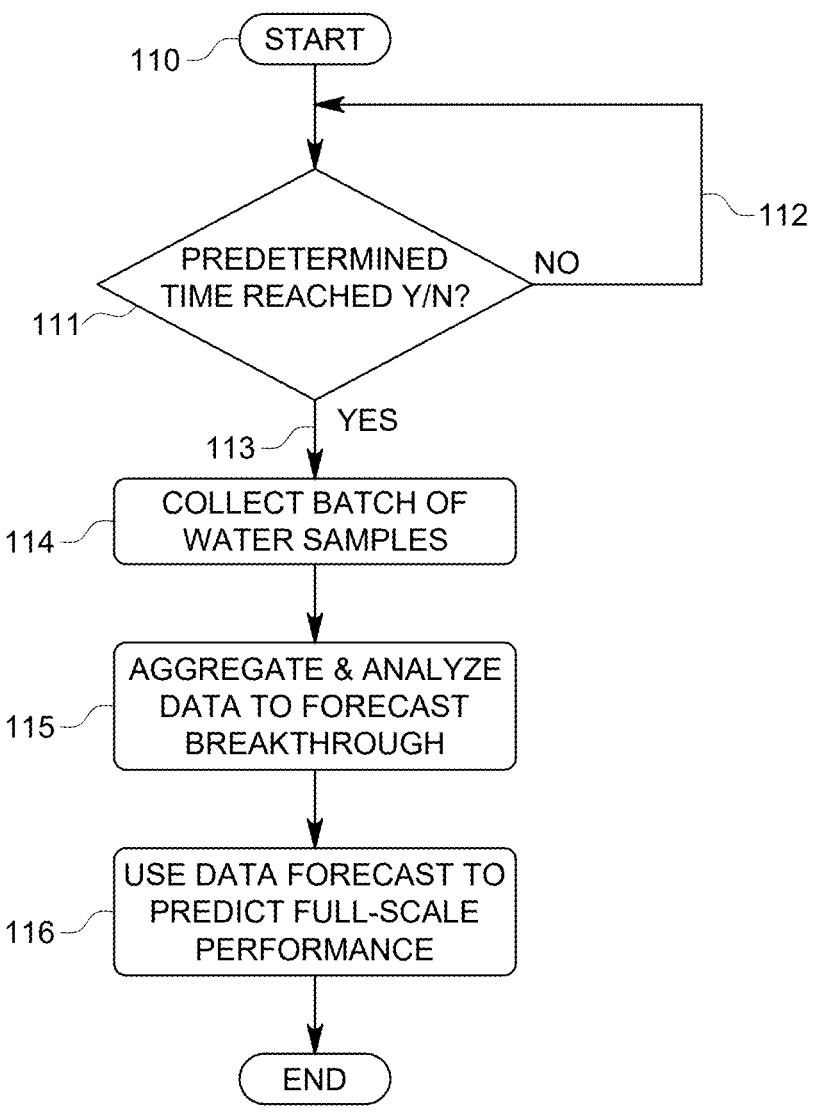
FIG. 2 is a flow diagram illustrating an exemplary implementation of a method according to the invention.

Referring to FIG. 2, an exemplary embodiment according to the invention is depicted illustrating a process flow diagram of an exemplary implementation of the invention where the time duration of the pilot is fixed ahead of the pilot by design. With the fixed time duration, samples are collected as a batch when that time expires, per the designated fixed time duration for the collection. Once the samples are collected, then all of the collected samples are analyzed to establish a profile and forecast the breakthrough. The forecast is correlated to the anticipated full scale performance. Typically, the breakthrough forecast determines the technically usable sorption capacity of the particular adsorptive material or media. According to the methods of the invention, a time duration for sample collection is set, and samples are collected within this time duration. In FIG. 2, block 110 marks the start of the process, where the process commences. At the commencement of the process, the water flow is permitted to flow through the filter media that is contained within the column (or columns) or pressure vessel/vessels. A predetermined time is designated for carrying out the sample collection, and samples continue to be collected until the predetermined time is reached, block 111. The decision line 112 shows the time duration has not been reached, and samples continue to be collected. The decision line 113 represents the condition when the time duration has been reached, and therefore, the batch of the water samples is collected, block 114. The next step is to aggregate and analyze data to forecast breakthrough, block 115. Once the breakthrough forecast has been determined, block 115, then the data forecast is used to predict full-scale performance, block 116. With the prediction using the sample collection, block 114, and the aggregation and analysis of the data from the samples collected, block 115, the full-scale performance prediction may be determined, block 116.

Figure 3:
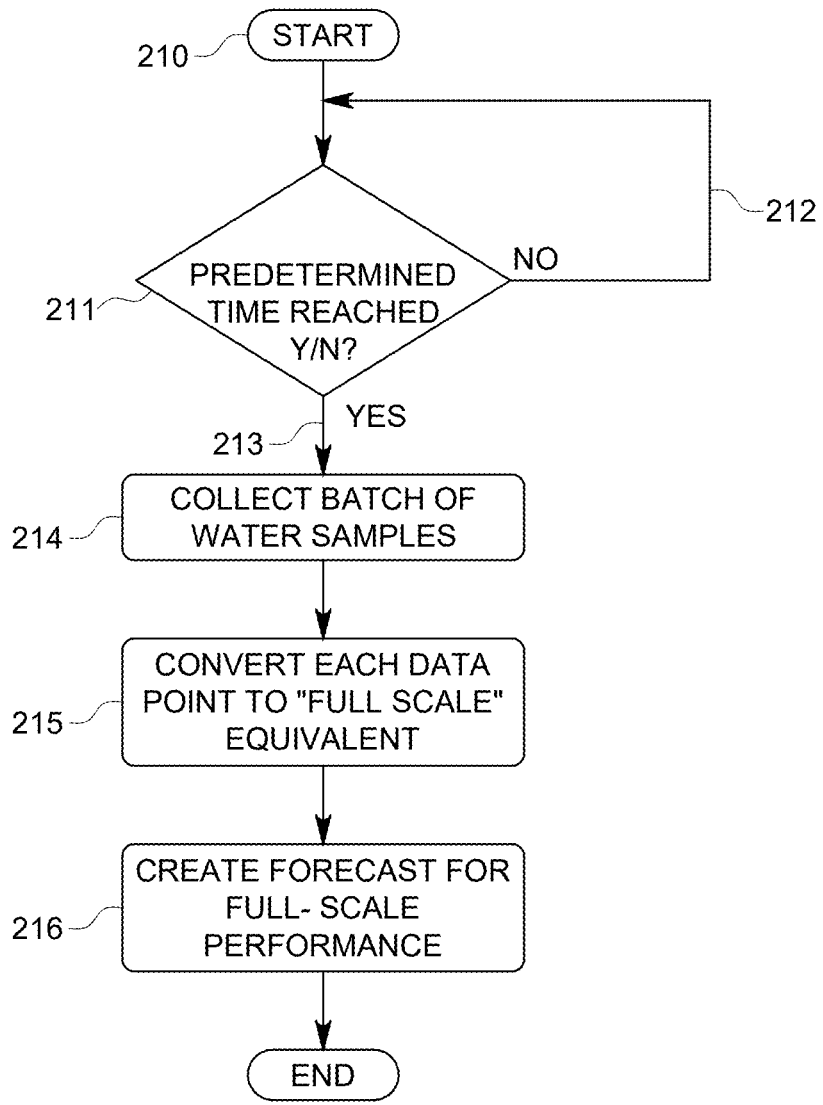
FIG. 3 is a flow diagram illustrating an alternate embodiment of an exemplary implementation of a method according to the invention.

Referring to FIG. 3, a flow diagram illustrating an exemplary implementation of an alternate embodiment of a method according to the invention is shown, and represents an optional configuration of the inventive process where the correlation to anticipated full-scale results is done ahead of the aggregation of data to establish a profile and forecast breakthrough. In other words, each data point in the batch is transformed to the anticipated full scale values and then aggregated. Then the full scale predicted values are forecasted to predict breakthrough at full scale. In FIG. 3, block 210 marks the start of the process, where the test commences. At the commencement of the process, the water flow is permitted to flow through the filter media that is contained within the column (or columns) or pressure vessel/vessels. A predetermined time is designated for carrying out the sample collection, and the test continues until the predetermined time is reached, block 211. The decision path line 212 shows the time duration has not been reached, and samples continue to be collected. The decision path line 213 represents the condition when the time duration has been reached, and therefore, the batch of the water samples is collected, block 214. The next step is to convert each data point to a "full scale" equivalent, block 215. Once the conversion is carried out, block 215, then the full-scale performance is forecasted, block 216. The full-scale performance forecast may then be derived from the processes of the invention, using the quantity of the filter media within the column (which is known based on the amount added to the column), the volume of the column, the water flow rate (which may be of water entering and/or exiting the column). PFAS concentrations of the test water, and the PFAS concentration for each sample. Further depiction of a determination is represented in the plot shown in in FIG. 7. In the example depicted in FIG. 7, the threshold ppt value is shown as 4 ppt, and is therefore representative of a predefined or assigned regulatory limit (e.g., federal, state and/or municipality), or may be another predetermined set limit. Although 4 ppt is shown as a representative threshold limit, the threshold may be any suitable threshold value according to law or regulation, or other designated value, and may change from time to time, location, special situation, or which may be set by the user. Typically, the filter media breakthrough evaluates the filter media for effectiveness in filtering PFAS from water or wastewater to meet the regulations in effect for that water being tested.

Figure 4:
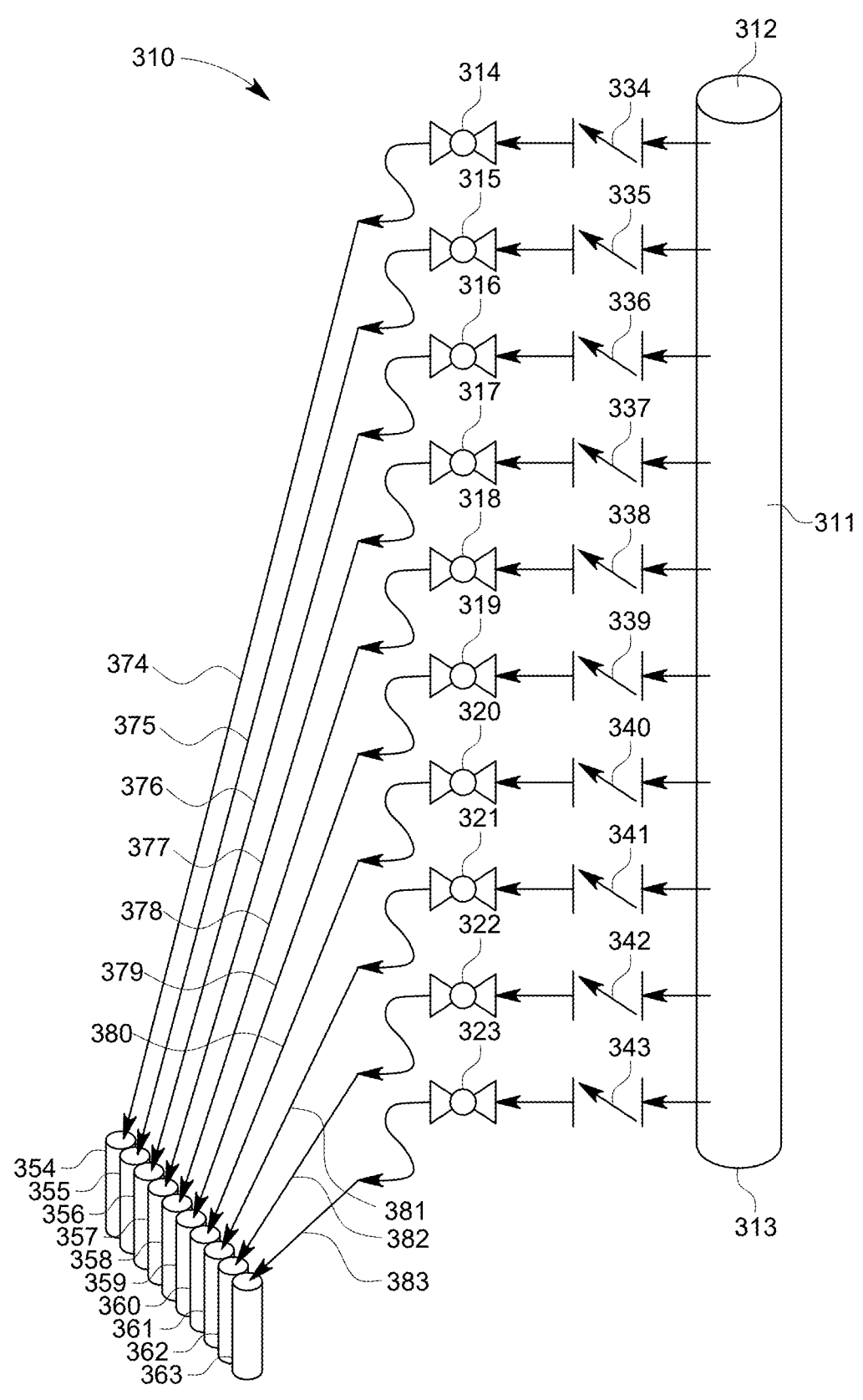
FIG. 4 is a schematic illustration showing an implementation of the invention in a multiple sample port per column configuration.

Referring to FIG. 4, a schematic illustration showing an implementation of the invention in a multiple sample port per column configuration. This figure shows how a single column of media can be tested where a batch of samples is collected from numerous sample points throughout the height of the column. This approach can be repeated for each media being tested. The arrangement 310 shown is an exemplary configuration comprising in schematic representation, a media column 311 having an inlet 312 and an outlet 313, with a plurality of sampling valves 314-323 arranged in fluid connection with the column, and being shown at different locations with respect to the length of the column 311, which is represented in a vertical position having a column height between the opening 312 shown provided at one end of the columns 311, and the outlet 313 at the other end of the column 311. The valves 314-323 are shown in a preferred exemplary arrangement controlling the flow of water from the column 311 at different outlet heights along the column 311. In reference to the column orientation in FIG. 4, which is vertical in the illustration, shown with the arrangement of valve sampling relative to the vertical position of the depicted column 311. The valves 314-323 preferably comprise taps that regulate the flow of water from the column to provide collection of the water flow from the column 311. The column 311 holds media disposed therein, which preferably is a type of filtering media that is designed to filter one or more contaminants from the water flowing into the column 311, which in this example, is referenced as the source water. The source water may be water from any source that is to be analyzed in accordance with the present systems, methods and devices. According to some implementations, the source water is water comprising or associated with a water supply or water treatment plant, or waste water treatment plant, or other water source that is desired to be monitored and analyzed. In the illustration depicted, the plurality of valves preferably are configured to be manual or automatic valves (e.g., such as an electronically controlled valve), and are shown associated with a respective plurality of ports 334-343 provided on the column. The ports 334-343 may comprise any suitable connection and one or more flow lines, such as, for example, pipes, tubing or other fluid conduits, or a direct connection between the respective plurality of valves 314-323 and the respective plurality of ports 334-343 may be made. The valves 314-323 preferably control the distributions from each of the respective ports the port locations on the column for distribution to a collection container. A respective plurality of sample containers or vials 354-363 are shown and are disposed to receive a sample from the column at a respective height along the column 311, which in this depiction is from a respective one of the plurality of valves 314-323. The containers 354-363 may comprise any suitable container including for example, jars, vials, bags, or other suitable containment that can hold the water sample. Preferably the sample container, as well as the valves and any conduits, such as lines, pipes or fittings are made from a non-reactive inert material which will not react with the water source or any substances in the water source including for example, any anticipated contaminants, such as for example, PFAS. In the arrangement depicted, there is a sample container per sample tap or port 354-363. The sample containers may be fitted with a suitable cover or port that allows direct connection or connection through a suitable fluid conduit to one of the respective valves 314-323. For example, the sample containers 354-363 may be situated at the end of one of the respective valves 354-363, or may be fitted with a port that accommodates a fluid carrier such as the respective lines 374-383 represented in the drawing. The water source flow direction is represented by arrows in the drawing. Although a number of valves are shown along the column 311, the number of samples and heights or positions along the column 311 may comprise any suitable arrangement of differently located valves to provide a sampling from different residence durations that each sample has within the column. For example shorter duration column residence, is exemplified by the valve 314 in the position closest to the water source inlet, and therefore the sample take from this valve 314 would have the least amount of contact with the filter media that resides within the column 311. Likewise, the valve 323 in the position closest to the water source outlet, and therefore the sample take from this valve 332 would have the greatest amount of contact with the filter media that resides within the column 311. The other valves would have contact durations between the first valve 314 and the last valve 323. Although the arrangement shows ten valves and ports along the column 311, other numbers may be provided, and/or some valves may be sampled and others may not. The arrangement as shown in the exemplary embodiment provides a plurality of valves that may be sampled from one or more of the plurality respective port locations on the column. The column and/or media in the column may be changed out to test different media. For example, the column, lines, valves and any conduits may be cleaned prior to subsequent testing of different media. Alternatively, one or more arrangements may be constructed for different columns, similar to the column 311, where each arrangement is provided for testing different media within each different column, which can be carried out at the same time, or at different times.

Figure 5:
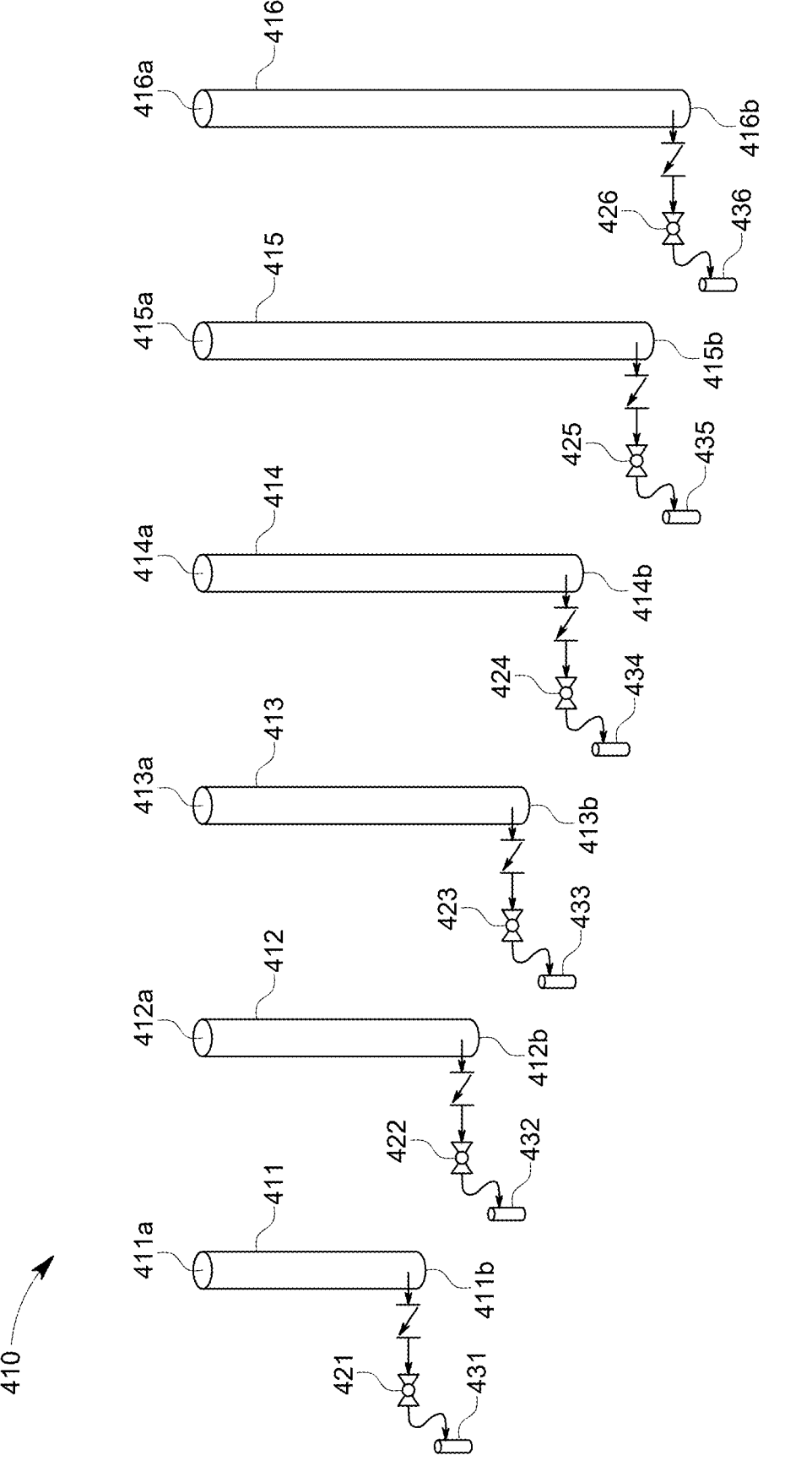
FIG. 5 is a schematic illustration showing an implementation of the invention embodied in an alternate configuration of a column array of various depths.

Referring to FIG. 5, an alternate configuration of the invention is depicted showing an alternate sampling collection arrangement 410, where instead of a single column with numerous samples taken along the height of the column (like what is depicted in FIG. 4), an array of columns of different heights are used. Then each sample for the batch is collected from the end of each column in the array. For the array, the same media is used throughout in each of the columns. The array is repeated for different medias being tested, with the different media being used, so each column has the same different media. The sampling arrangement 410 is shown depicting a plurality of columns 411, 412, 413, 414, 415, 416. Although six columns are depicted, there can be different numbers of columns, and the columns while shown in an arrangement from shortest to tallest in height can be in any arrangement. In the schematic illustration the plurality of columns 411-416 are shown having different heights or lengths, and preferably each contains the same media that is desired to be evaluated. Each column of the plurality of columns 411-416 therefore provides a different residence distance for water traveling through the column, and hence contact with different amounts of the media (based on the column height). Each column 411, 412, 413, 414, 415, 416 is shown having a respective inlet 411*a*, 412*a*, 413*a*, 414*a*, 415*a*, 416*a*, and a respective outlet 411*b*. 412*b*, 413*b*, 414*b*. 415*b*. 416*b*. A flow regulator, such as a valve. 421, 422, 423, 424, 425, 426 is shown provided in association with each of the respective columns 411, 412, 413, 414, 415, 416. The water flow enters the column inlets 411*a*. 412*a*. 413*a*. 414*a*. 415*a*. 416*a*, and flows through the column contacting the media within the column, and exits the column through a respective outlet 411*b*, 412*b*. 413*b*, 414*b*, 415*b*. 416*b*. However, the system may be controlled to take samples from one or more, and preferably each of the columns of the arrangement of columns, which as illustrated, provides for sampling at different levels of the source water. As illustrated, the plurality of valves, 421, 422, 423, 424, 425, 426 preferably are connected to allow the flow of source water within a respective column to flow directly or via some type of fluid conduit such as a line or pipe, into a respective a sample container 431, 432, 433, 434, 435, 436. The samples are collected, and analysis may be conducted in accordance with the methods disclosed herein.

The sampling arrangements depicted in FIGS. 4 and 5 may be used to carry out the methods disclosed herein, including the methods represented by the flow diagrams of FIGS. 2 and 3.

Figure 6:
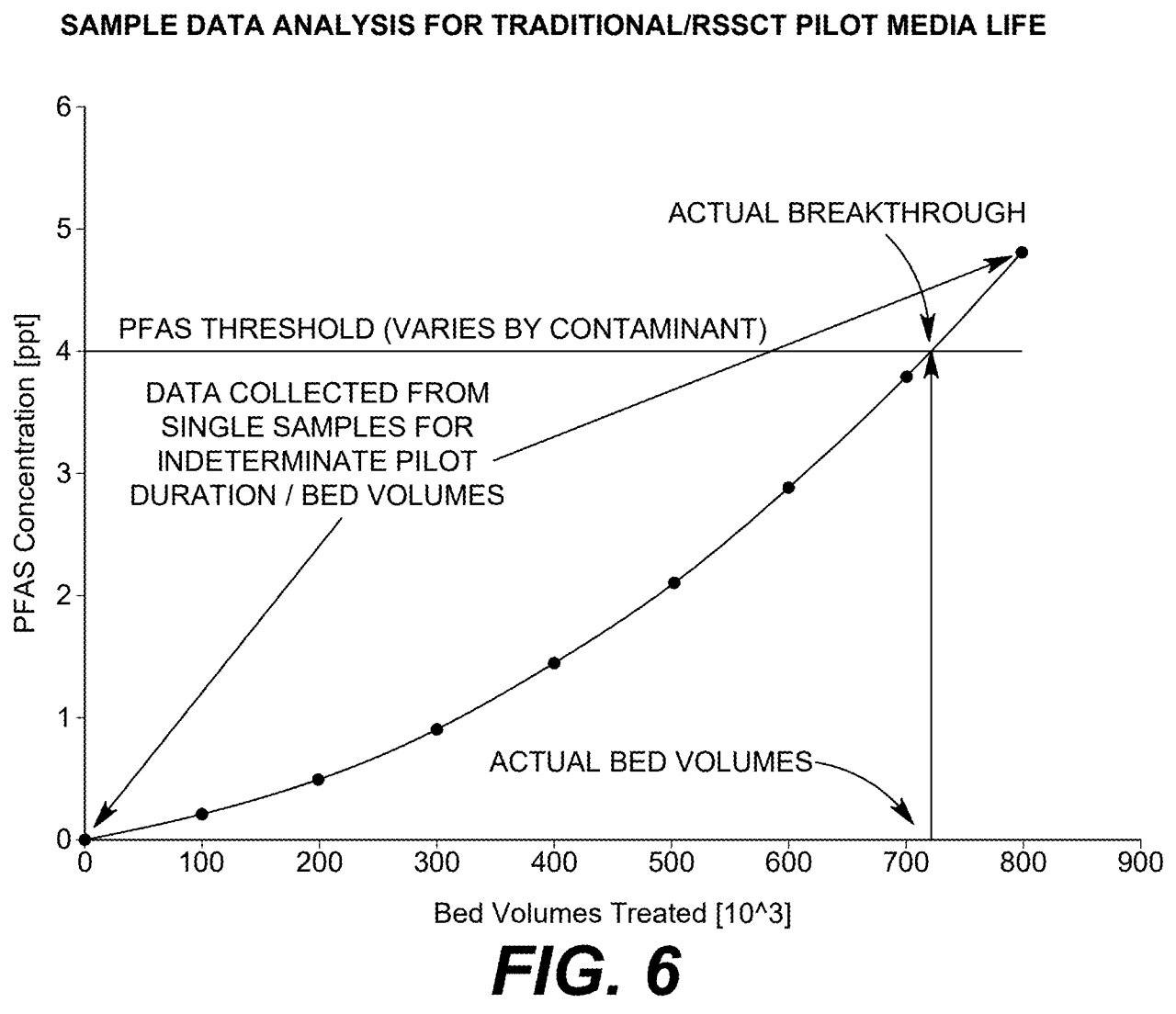

Referring to FIG. 6 shows a graph of a plot for sample analysis for traditional pilot (TPT) and RSSCT, showing bed volumes versus PFAS concentration. FIG. 6 shows how a traditional pilot or RSSCT ends after breakthrough occurs, with a final sample collected past the breakthrough threshold. There can be a considerable amount of time between single samples and therefore a considerable amount of time after breakthrough occurred before it was detected by a single sample collection. That extra time past actual breakthrough (tP) before detection is waste in the form of inefficiency which the invention addresses via the batch sample process and forecast. The breakthrough first detection of PFAS may be below the regulatory limits (of federal and/or state regulations, for example, where the state regulation is a stricter standard, lower threshold for contaminants than the federal limit). The regulatory limits. e.g., federal or state, or municipality, may determine the threshold value. According to some other embodiments, the limit may be a user defined limit, e.g., which preferably is below the regulatory limits. Variation in detection also may be dependent on the lab capability, if for example, one wanted to forecast breakthrough at a more proximal time frame to the breakthrough. This may be done using sample analysis that collects and analyzes samples over a narrower time period.

Figure 7:
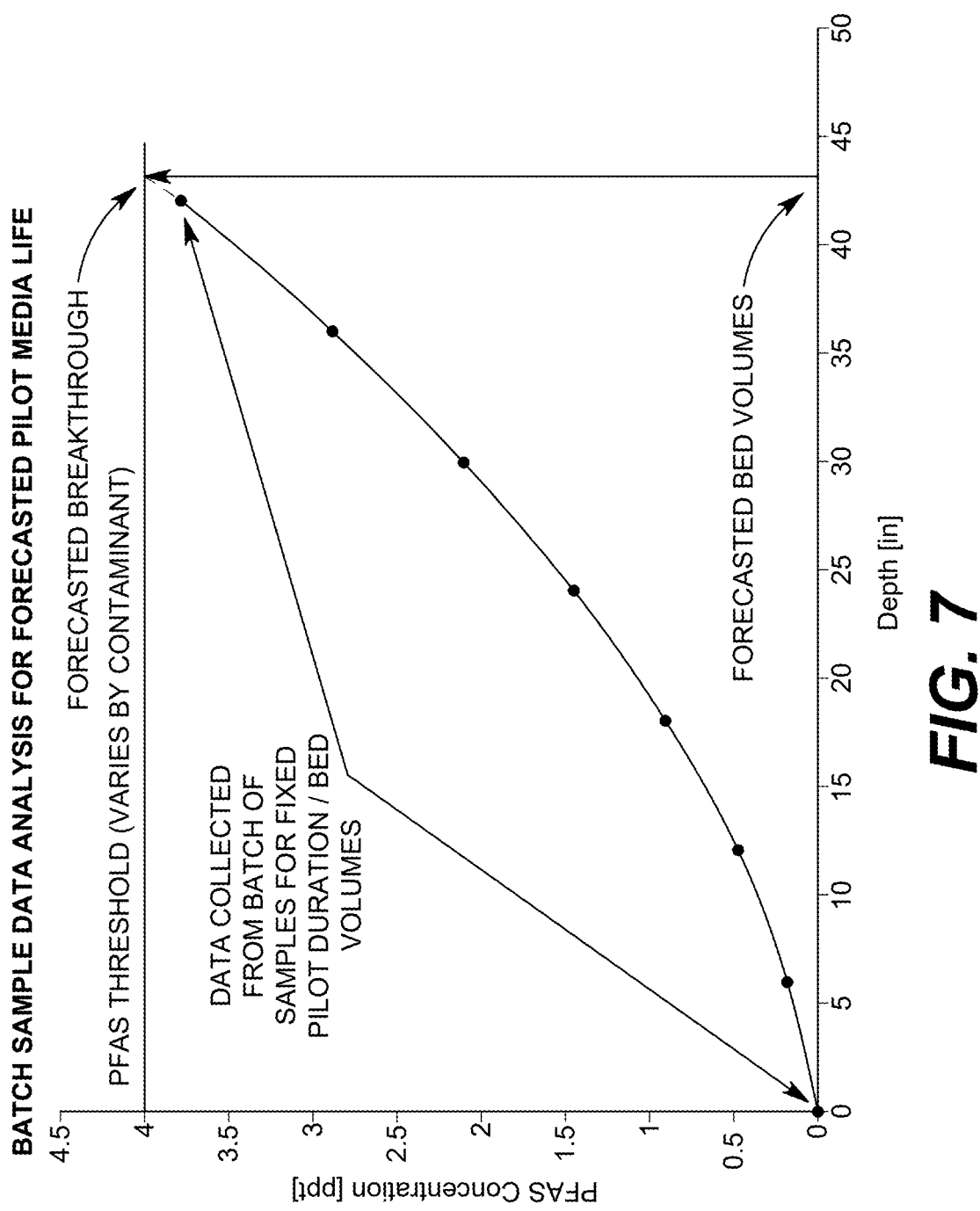
FIG. 7 is a graph of a plot for an example analysis for the method and apparatus of the invention, showing depth versus PFAS concentration.

FIG. 7 is a graph of a plot for an exemplary sample analysis for the method and apparatus of the invention, showing depth versus PFAS concentration. FIG. 7 shows how a profile from a batch of samples takes using the methods and devices of the invention is used to forecast breakthrough, which further removes time required for the pilot test of the inventive methods to be conducted compared to traditional pilots (TPT) and RSCCTs. The time saved in the invention compared to traditional pilots and RSSCTs comes from choosing a time duration appropriate enough to establish a sufficient number of data points for the forecast without spending unnecessary time running the pilot beyond the needed data points. For example, a plurality of sampling taps along a vessel may be provided, and according to some embodiments there may be 3 or more, and according to other embodiments and implementations the number of sample taps may be about 10 to 12 (or more) if desired. The number of sample taps on a column may be based on the media type being tested, and the dimensions of the column. This is achieved through the methods and apparatus shown and described herein. The invention also saves time compared to traditional pilots and RSSCTs by saving the wasted time that typically occurs in traditional (TPT) and RSSCTs where breakthrough occurs before detection by single samples. That is when the breakthrough occurs, the sample analysis that confirms the breakthrough takes place at a time after the breakthrough has occurred. FIG. 7 shows a plot for data collected from a batch of samples for fixed pilot duration and bed volumes of a filter media/medium. The media life is forecasted from the plurality of samples and the analysis represented by the plot shown in FIG. 7. The depth in inches (along the x axis) shows the filter media and preferably this may be correlated with a volume of the filter media residing in the column(s). The y axis shows the PFAS concentration in ppt (parts per trillion). Although the PFAS threshold will vary based on the contaminant, from the plotted concentration values from analyzing each sample, the forecasted breakthrough can be determined. This is the expected life of the media, which is the forecasted point that the media being tested will provide the desired level of PFAS filtration (for example, to remain below or not exceed the threshold value for the contaminant).

Figure 8:
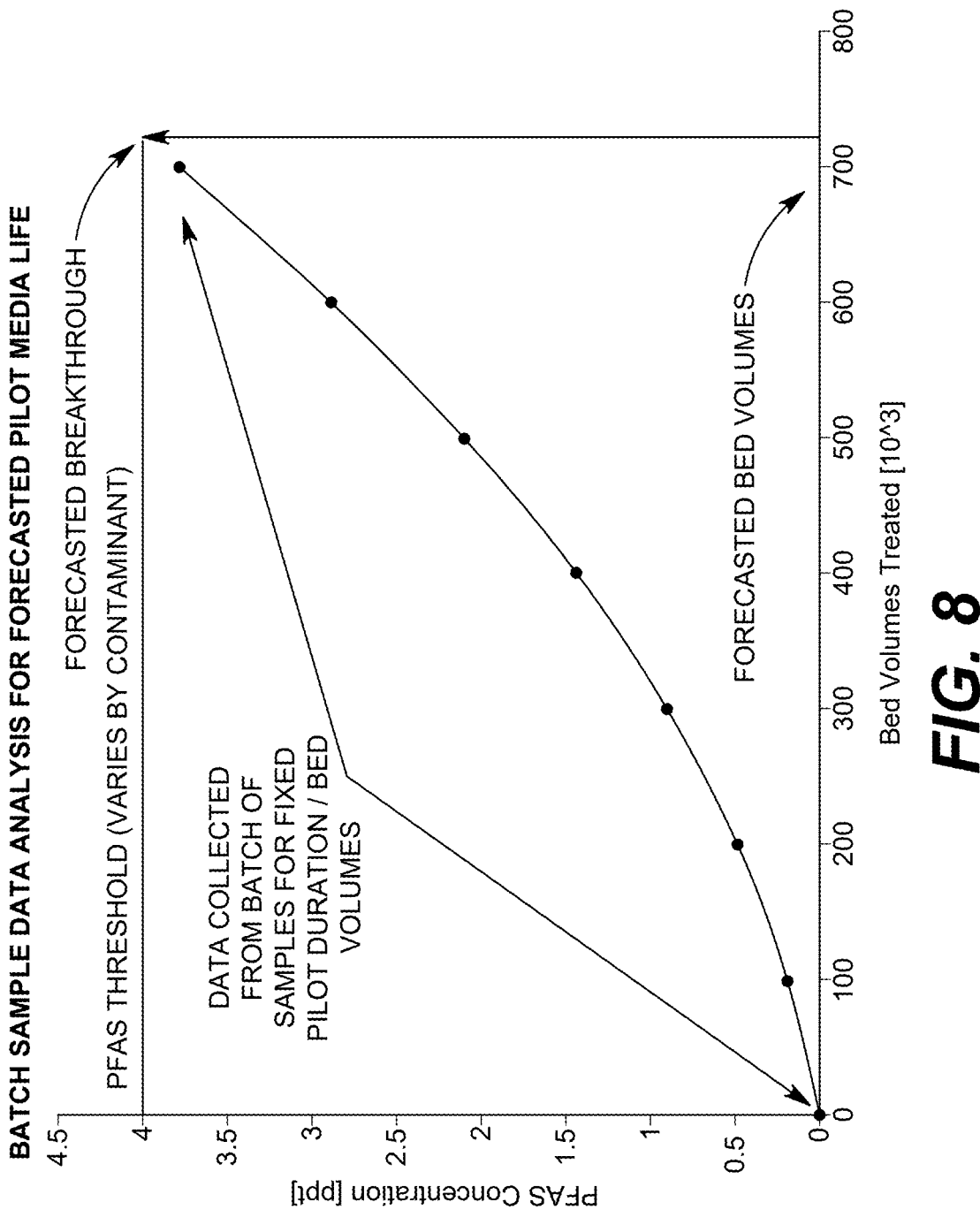
FIG. 8 is a graph of a plot for of an example analysis for an alternate implementation of the method of the invention, showing bed volumes versus PFAS concentration.

FIG. 8 is a graph of a plot of an example analysis for an alternate implementation of the method of the invention, showing bed volumes versus PFAS concentration. FIG. 8 shows an exemplary implementation of the method of the invention being applied to an alternate process configuration where the batch sampled data is first transformed to anticipated full scale values, and then the forecast of breakthrough is applied to the anticipated full scale values.

The graphs illustrated in FIGS. 7 and 8 depict a best fit equation, which in these examples are shown as best fit curves, for the plot of sample where the contaminant concentration is shown in ppt on the y axis, and where the volume of filter media in a pilot column or pilot vessel is represented along the x axis. The best fit equation is an equation that minimizes the error between the sample data points for the pilot. In the exemplary depictions, the best fit equation is shown represented by a best fit curve that provides error minimization for the representation of the set of sample concentrations for the different bed volumes. The best fit equation preferably minimizes the difference between the observed data and the predicted values based on the equation for the curve or line. In the examples depicted in FIGS. 7 and 8, a parabolic exponential function provides a best fit equation, resulting in the best fit curve depicted. A best fit equation may relate the samples from the pilot (contaminant concentration and filter media bed volume), to generate the breakthrough point, which is a forecasted breakthrough (where the filter media capacity for the water source, and flow total through the filter is reached). The forecasted breakthrough is shown in FIGS. 7 and 8 at a location where the samples have not exhibited a breakthrough in the filter media associated with each respective sample vessel or column.

Figure 9:
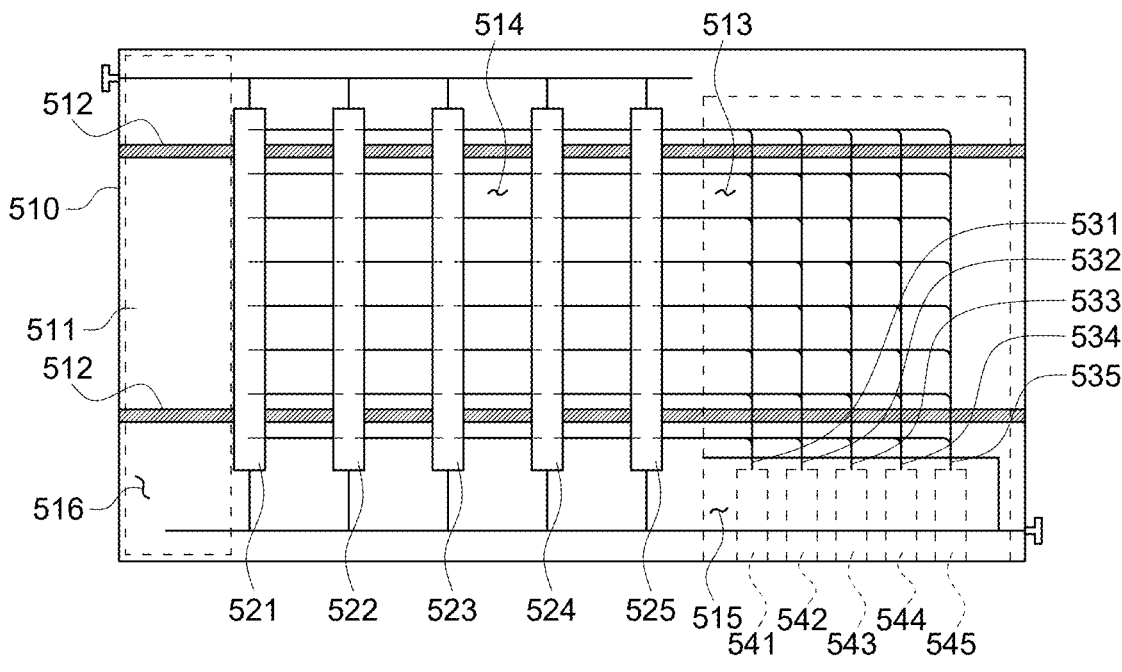
FIG. 9 is a front view showing a schematic illustration representing an exemplary arrangement of a mobile or packaged pilot system according to an embodiment of the invention.

FIG. 9 is a front view showing a schematic illustration of a front elevation view of an exemplary arrangement of a mobile or packaged pilot system according to an embodiment of the invention. The arrangement 510 is shown comprising a skid 511 that contains several important areas including space for the media columns 521, 522, 523, 524, 525, for each media being tested (which preferably is loaded in one of the respective columns), racking 512 to support the media columns 521, 522, 523, 524, 525, area(s) 513, 514 for piping or tubing from each sample tap 531, 532, 533, 534, 535 to each sample vial or jar 541, 542, 543, 544, 545, area(s) 515 for sample collection, and area(s) 516 for optional electrical control systems. The mobile or package system can also contain several windows to view equipment and access panels to reach equipment and samples. The package system also contains provisions for hooking up water from the pilot site and optional electrical when controls are included.

For example, according to some embodiments, the method may be carried out with control systems, which may comprise manually operable valves for sample collection, or in some embodiments, may comprise an electronic control system. For example, an electronic control system may include one or more processors, microprocessors, controllers, integrated circuits, with software or other embedded logic that includes instructions for instructing the processor to carry out operation of the valves, collection of the samples. The electronic collection may be based on time or some other metric. In accordance with embodiments, the valves may be electronically operated to open when the test is being conducted, or on a planned test timing (such as 24 hours, or within a certain period of a day or days), and to close either when an operator desires to conclude a test, or electronically. The apparatus may comprise and the methods may be implemented electronically where the sampling is controlled by controlling the flow of water through the columns (e.g., through an inlet and/or an outlet) and from the column to a sample container, through one or more sampling valves. According to some implementations and embodiments, the apparatus is manually operated. However, according to some alternate embodiments, the apparatus is electronically operated. The apparatus may further include circuitry, sensors, one or more processors, and one or more memories, as well as software, firmware, or other embedded logic, containing instructions for operating the valves, and monitoring the sample contents for volume or other information. The circuitry may include or be supported by one or more suitable software programs, which can be stored on or otherwise provided by any kind of data carrier, and which might be executed in or by any suitable data processing unit of the device, such as a processor, microprocessor, controller, microcontroller, integrated circuit, embedded logic or other suitable technology. The device electronics may include hardware, or one or more programs stored in non-volatile memory in controlling hardware, that may be in the form of embedded software, or in hybrid form. i.e. by means of combination of any of the above components. The device electronics may include instructions for carrying out the operations of the device electronics, and capturing, communicating, exchanging and processing the information about the method for obtaining the sample collection from the water source, through any implementation in software, firmware (embedded software) and/or hardware (for instance by an ASIC, application specific integrated circuit), or other means. Additionally, processing algorithms for the sampling apparatus can be encoded in software, firmware, embedded within silicon-based logic devices, or combinations of such approaches.

Figure 10:
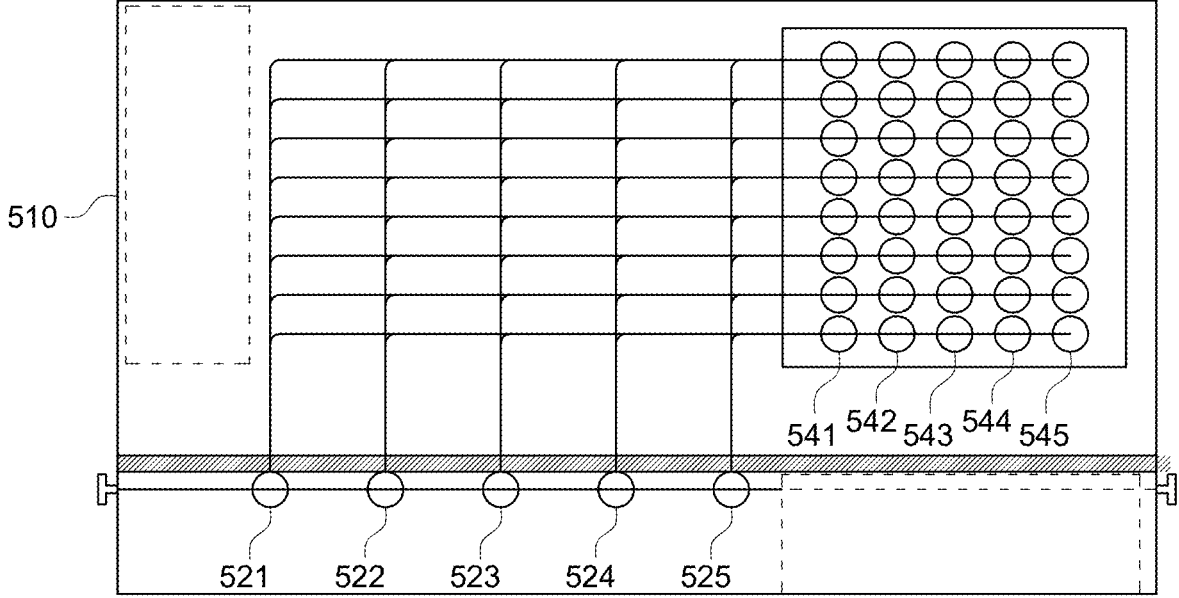
FIG. 10 is a top plan view of a schematic illustration of the mobile or packaged pilot system shown in FIG. 9.

FIG. 10 is a top plan view of a schematic illustration of the mobile or packaged pilot system 510 shown in FIG. 9 showing an exemplary arrangement of a mobile or packaged pilot system for the invention. According to the exemplary illustration the arrangement, there are arranged in this exemplary configuration a plurality of columns 521, 522, 523, 524, 525, each having media therein, and each having a plurality of taps through which fluid from the column may be fed to and collected in a sample container. In FIG. 9, the elevation view is shown, and in FIG. 10, there are a total of eight tap location shown provided on each of the columns, though the number of taps may be greater or fewer than the eight shown in this exemplary embodiment. The tap locations on each column are provided at different column heights. A number of sample collection containers are shown, and in addition to the first row of sample vials or jars, such as those 541, 542, 543, 544, 545 shown in FIG. 9, the sample array includes seven additional rows containing five sample vials or jars in each row.

Figure 11:
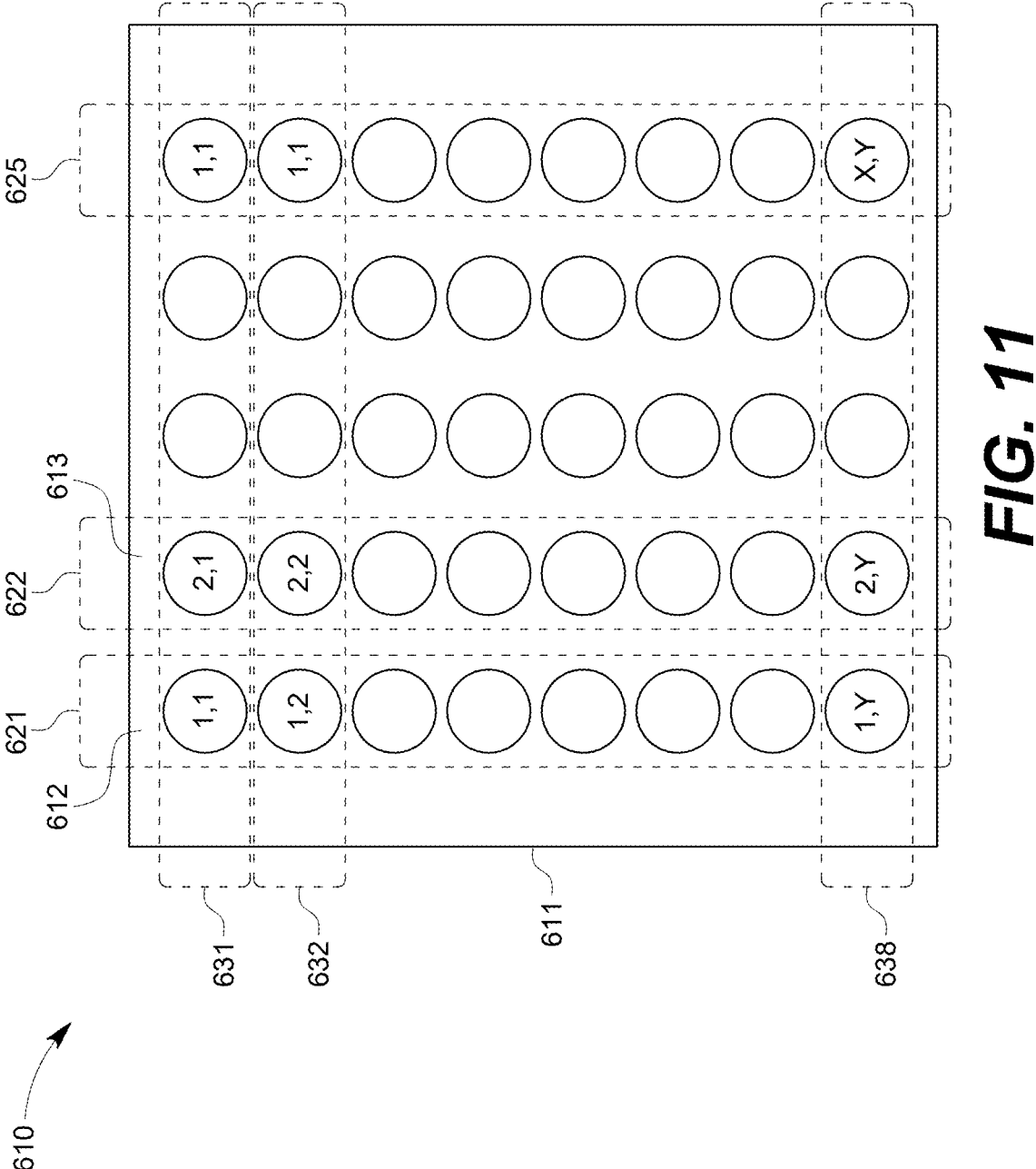
FIG. 11 is a top plan view of a schematic representation of an example of a batch sample collection arrangement according to the invention.

Referring to FIG. 11, a top plan view of a schematic representation of an example of a batch sample collection arrangement 610 according to the invention. In the arrangement 610, each sample tap is configured to have a corresponding sample jar or vial in the batch. In the skid 611, the sample jars or vials 612, 613 . . . n, can be located throughout the skid 611 to minimize piping and appurtenances. Alternatively, the entire sample batch can be located in a single area A1, as shown here to facilitate easier sample collection at pilot completion. In the arrangement 610 illustrated, the media column 1, 621, media column 2, 622, . . . media column 5, 625, are shown in a first row of the array, and the sample tap 1, 631, sample tap 2, 632 . . . sample tap 8, 638, are shown in a first column of the array. This is an exemplary arrangement to show a batch sample arrangement of sample collections where each sample vial depicted in the exemplary array of 40 samples, represents a sample from a column #, and tap #, thereby providing a collection from the different locations for the water source and filter media being evaluated. For case of reference, the first sample is abbreviated to represent sample column 1 and tap 1. Thereby providing the column and location on the column from which the sample was taken. Similarly, the next sample represented in the row going across is sample column 2, tap 1. The arrangement is set out in this exemplary order in this depiction.

The inventive methods may be carried out in accordance with implementations shown and described herein. According to one implementation, a Multiple Sample Port per Column-Automated Batch Sample Collection is employed. In this embodiment and implementation, one or more media types or varieties may be tested. For each media variety, a single column of media is used. Along the height of the column are multiple sample ports from which samples may be drawn. A suitable procedure for tracking the time for sampling, or between sample draws may comprise manual operation of the sampling through operation of the sampling valves at the column sample taps. Alternatively, the sample valves may be configured with electronic controls or comprise electronic valves that may be electronically operated, either by a user, or autonomously on a circuit based on time, and/or based on flow totalization, or other routine programmed into the circuitry. According to one implementation, when time elapses and/or a volume threshold has been achieved (tracked via digital controls, analog timer circuit, manually tracked, flow totalizer, etc.), water is drawn into every sample port and sample vials for the column via automated flow control valves actuated based on the timer or an operator signal to ensure flow rate does not cause short circuiting of the test media. For example, the flow passing through the system and each column or tank is measured and used to determine when a designated flow has passed through the system (preferably through each column or tank containing the filter media being evaluated). The flow rate must be suitable so that the flow is representative of contact time between the water source and the filter media in the column. For example, if the sampling flow through the valve is too swift, then the water source may flow through the column and out of the sample tap without having or with minimal time in contact with the filter media. Similarly, where the flow rate is too slow, then the filter media contact will be overrepresented, and may lead to inaccurate results. The same source ports are connected to vials to contain the samples. This occurs for every media variety being piloted.

According to another implementation, Multiple Sample Port per Column-Manual Batch Sample Collection is employed. For each media variety, a single column of media is used. Along the height of the column are multiple sample ports. When time elapses (tracked via digital controls, analog timer circuit, manually tracked, etc.), an operator manually actuates a series of valves to draw water into all of the sample ports (and vials) until the complete batch of samples is taken. This occurs for every media variety being piloted. Therefore, there may be a plurality of the media column and sample collection arrangements representative of each media being piloted. In other words, the exemplary arrangements in FIGS. 4-5 and 9-11 may be duplicated for the number of media types being tested, with each media variety or type being tested having its own sample collection arrangement of columns and sample vials.

According to another implementation Column Array of Various Depths-Automated Batch Sample Collection is employed. For each media variety, multiple columns of various depths per media are used. One exemplary depiction of this implementation is shown in FIG. 5, where the columns are provided at different depths. The arrangement in FIG. 5 represents one apparatus and arrangement for carrying out the method, and the implementation of this method is not limited to the apparatus or arrangement shown in FIG. 5. At the bottom of each column is the sample port to fill the sample vial. When time elapses (tracked via digital controls, analog timer circuit, manually tracked, etc.), water is drawn into every sample port and sample vials for the column via automated flow control valves actuated based on the timer or an operator signal. The sample ports are connected to vials to contain the samples. This occurs for every media variety being piloted.

According to another implementation. Column Array of Various Depths-Manual Batch Sample Collection is employed. For each media variety, multiple columns of various depths per media are used. At the bottom of each column is the sample port to fill the sample vial. When time elapses (tracked via digital controls, analog timer circuit, manually tracked, etc.), an operator manually actuates a series of valves to draw water into all of the sample ports (and vials) until the complete batch of samples is taken. This occurs for every media variety being piloted. This is similar to the varied depth implementation discussed above, and represented by an exemplary apparatus and arrangement in FIG. 5.

The methods of the invention do not prescribe the components required to implement the process provided here as there is a wide variety of valves, tubing, pipes, electrical controls, racking, and sample retaining hardware that can be combined to achieve the batch sample process benefits described here. However, according to some embodiments, inventive apparatus and arrangements are provided. The invention also does not prescribe the number of sample points per media being tested, and dimensions of the system. Preferably, the number of samples per media being tested are sufficient to allow for enough data to establish the profile of PFAS propagating through the media and forecast breakthrough. According to some embodiments, the dimensions of the media columns may be representative of the full scale vessels. The only requirement for the process provided in the invention is to choose the pilot duration or flow totalization such that breakthrough of the final sample point does not occur which would compromise the results of the pilot because the batch of samples would be collected without knowing when breakthrough occurred. Apart from that requirement and those recommended design considerations, the process in the invention can be implemented with any of the components previously mentioned in either a fixed system, fixed skid, or mobile unit for rapid deployment at scale.

The invention also does not prescribe the method of correlation between the batch sample process with breakthrough forecast and the anticipated full scale bed volumes as a wide variety of models can be employed to achieve the benefits of this invention. The models that can be employed include but are not limited to empirical models, mechanistic models, and machine learning based approaches.

Mobile or Package System

According to preferred implementations and embodiments, the process of the invention provides users with a discrete pilot test because of the batch sample collection method. In other words, users can set up a pilot test according to the methods of the invention, leave, and return to collect the batch of samples at the end of the pilot test. No other interaction between start and finish for the subject invention pilot test is required. Because the inventive methods of the pilot test can be unmanned throughout the duration of the test, unlike traditional pilots (TPT) or RSS-CTs, the inventive methods are well-suited for deployment at scale as a mobile or package unit. Apart from use in pilot testing, the subject invention can be deployed as a package system left installed at a treatment facility for use in monitoring full scale performance. The mobile or package system is represented by embodiments illustrated. According to some embodiments, a single contained apparatus that includes one or more components, such as columns, media, sample taps, sample collection containers, may be provided in a housing unit (or multiple housing units that contain one or more or all of the components). According to some implementations, the housing unit may include manual controls, so an operator (human operator) may operate the valves for the sampling taps to deliver samples into the sample containers. According to some other embodiments, the valves may be automatically controlled through electronic controls. The electronic controls may be operated by a human operator, or alternatively, the electronic controls may be programmed to take samples at one or more or periodic, or any arranged or predetermined time intervals.

Therefore, the arrangements depicted in the figures herein may be provided as a unit that comprises a sampling device. The unit may be a manually operable unit for collecting samples, or may be an electronic unit, where samples may be collected based on the electronic operation of the valves and sample ports. The electronic unit may further comprise embodiments that may be autonomously operated with programming to collect samples using the methods disclosed herein. For example, a timed collection circuit may be employed to operate the sample valves or taps to obtain samples. Flow rates also may be designated, or the flow rates corresponding with the valve operation (open or percentage open) may be based on the flow rate of the water source through the sample column. For example, flow sensors may be provided on the columns (inlet, outlet or both) to determine the flow rate and total flow through the column (as some media can affect the flow rate and may change over time as the media is exposed to the water source). The flow rate through the column determined from the flow sensors may therefore be used to adjust and regulate the flow rate from the sample taps. For example each sample tap may have an electronically operable valve, and the valve may be controlled as to open closed, or some degree of open, to provide a suitable flow rate.

According to embodiments of the invention the water samples of the filtered water from each of the samples taken are analyzed for a concentration of the contaminant or contaminants that the filter media is being evaluated for its effectiveness in filtering those contaminants from the water source or wastewater source. A suitable analyzer compatible for the contaminant of interest is used. Some examples of analyzers and techniques for determining contaminant concentrations, such as for example, PFAS concentrations in water or wastewater, include mass spectrometers, chromatography analyzers (e.g., UHPLC, HPLC. GC), including for example, liquid chromatography-mass spectrometry (LC-MS/MS), gas chromatography-mass spectrometry (GC-MS), high-resolution mass spectrometry (HRMS), and electrochemical sensors like voltammetric and potentiometric sensors.

The pilots disclosed herein are designed to simulate the full scale operation for a water source that is to be filtered using the filter media being evaluated. The hydraulic load rate for the pilot filtering of contaminants is applied in the pilot so that the pilot simulates and represents the eventual filtration of the water or wastewater with the filter media, which for most deployments will be a larger or full scale versus the pilot. The hydraulic load rate may be selected for the pilot based on the filter media supplier (or manufacturer) recommendation for a particular contaminant. The columns or vessels used in the pilot that contain the filter media are provided having a diameter that provides contact time with the filter media at the flow rate of the water or wastewater for which the filter media effectiveness is being determined in the pilot. The column diameters therefore can be selected to represent a hydraulic load rate that also will be expected for the full scale operation using the same filter media type. The pilot filter media is the filter media type that the larger or full scale system will use. The filter media type may include a single filter media type, or may include one or more types (e.g., GAC and/or ion exchange), and the pilot filter media type also may include a single filter media type, or may include one or more types (e.g., GAC and/or ion exchange) that the full scale filter media will use. The media in the pilot columns or vessels while the same type is used for pilot, while fresh filter media of the same type is used for the filtration of the water source or wastewater source.

Although the filter media has some known capability to filter the contaminant or contaminants for which it is selected to filter from the water source, there are challenges in a water or wastewater system, that are unique to that water and which may therefore alter the filter media effectiveness. For example, filter media may have an affinity to filter the one or more designated contaminants, but may not be selective to only those, and may filter other substances as well, potentially using a portion of the filter media capacity. While according to some other filter media types, the filter media affinity may be highly selective to remove only the designated contaminant. The water source or wastewater source therefore may contain some or no level of filter media competing substances, and therefore, the filter media effectiveness must be considered for each water source and/or environment. The pilot determines the effectiveness of the filter media for the water source or wastewater source that the filter media will be deployed to filter (to remove one or more contaminants and provide a filtered water output that meets or exceeds a threshold contaminant level, which may be a target selected by the user, a municipality, or other desired goal or requirement).

The invention also provides a method for removal of contaminants from a water source or wastewater source. This is carried out by filtering the water of the water source or wastewater source using filter media whose effectiveness is determined through the pilot, to provide filtration of the water or wastewater to the desired level (e.g., having level of one or more contaminants in the filtered water output from the filter system that is at or does not exceed the designated level). According to an exemplary implementation, the filtering of the one or more contaminants from the water source or wastewater is carried out by flowing the water source or wastewater source through the filter system. According to an exemplary embodiment, the filter system comprises a contaminated water or wastewater inlet and a filtered water outlet. The filter system also has one or more vessels in communication with the contaminated water or wastewater inlet and the filtered water outlet. The filter media is contained in one or more vessels. For example, the vessel preferably has an inlet and an outlet, and the water enters the inlet and comes in contact with the filter media contained in the vessel, and then exits through the outlet.

The outlet flow may flow to another vessel with the same or different type of filter media, or alternatively, the outlet flow may flow to a conduit for collection, testing or use. The filter system and pilot may be used to provide potable water, or to treat water from a water or wastewater source so the filtered or treated water may be rendered safe for placement into the environment or returned or reclaimed for use. The filter media contained in the one or more vessels is effective to remove the contaminant or contaminants from the water source or wastewater source, and preferably is effective to maintain the concentration of the one or more contaminants at or lower than a designated concentration level for the one or more contaminants. The filter system provides an output of filtered water flowing from the filtered water outlet.

In the exemplary arrangement, the vessel or vessels have an inlet and an outlet, and at least one or more of the inlets of the one or more vessels comprises or is in communication with the contaminated water or wastewater inlet. At least one or more of the outlets of the one or more vessels comprises or is in communication with the filtered water outlet. The water flows into the contaminated water or wastewater inlet to be in flow communication with the filter media in one or more of the vessels. The filter media is effective to remove the one or more contaminants from the water source or wastewater source, by flowing the water source or waste-water source through an inlet of the one or more vessels, with the filter media contained in the one or more vessels being in fluid communication between the at least one contaminated water inlet and at least one treated water outlet. Water from the water source or wastewater source flows through the filter system. The flow may be managed by one or more valves that control the flow rate to allow the water or wastewater to have contact time with the filter media. The water source or wastewater source is flowed through the system at a flow rate to allow the flowing the water source or wastewater source that flows into the one or more vessels to have contact time with the filter media contained in the one or more vessels to effect the removal of the one or more contaminants that the filter media is effec-tive to remove. In the filter system design, hydraulic load rate and contact time are directly correlated to the flow rate. The effectiveness of the filter media, which is effective to remove the one or more contaminants from the water source or wastewater source, is an amount of the filter media that effectively filters the one or more contaminants from the water source or wastewater source, and removes the one or more contaminants from the water source or wastewater source, for a flow total amount of volume of the water source or wastewater source containing the one or more contami-nants that flows through the filter media contained in the one or more vessels of the filter system. The effectiveness of the filter media also is effective for the hydraulic load rate that the pilot samples and the larger scale filter will utilize. The flow rate and vessel size, as well as the filter media volume or depth in the column or vessel, are parameters that may be designated for the pilot and/or the full scale filter system to a hydraulic load rate.

According to some embodiments, the amount of filter media used in the filter system, which may be in a single vessel, or in a plurality of vessels (e.g., in a train of vessels or serial or parallel arrangement of vessels), preferably is the breakthrough volume of the filter media amount that the pilot provides. The pilot samples of the filtered water from the water source or wastewater source provide a forecasted breakthrough where the filter media has reached its capacity to filter the contaminants from the water source or waste-water source to a level that is lower than or equal to the designated level (contaminant concentration level). Accord-ing to some embodiments, the filter media volume for the filter system is the flow total volume of the contaminant-containing water source or wastewater source that the filter media is effective to remove contaminants from, and the flow total volume that is a breakthrough volume. The designed flow rate for the filter system takes place at the hydraulic load rate for the media being utilized and the one or more contaminants that are to be removed by the filter media. The breakthrough volume is obtained by the pilot, and may be used to provide flow scaling for the large scale or full scale filtering of the water source or wastewater source. For example, where the pilot is carried out for a specific media type, and to remove one or more designated contaminants from the water source or wastewater source, then the hydraulic load rate at which the pilot is carried out, may be scaled to the full or large scale filter system, which preferably uses the hydraulic load rate that the pilot has employed. The breakthrough volume for a filter media whose effectiveness for a water or wastewater source is generated using a pilot such as the pilots discussed herein and represented in the figures. A plurality of pilot vessels or columns are provided, and the pilot filter media is contained in the vessels or columns. According to some embodiments each pilot vessel or column has a filter bed or media space where the pilot filter media is contained. According to preferred implementations, the pilot vessels or columns contain the breakthrough or pilot filter media, and prefer-ably, at least some of, or each of, the pilot vessels or columns contain different amounts of breakthrough or pilot filter media.

The pilot filter media in each of the respective pilot vessels or columns provides a different contact duration between the water source or wastewater source and the pilot filter media. The different durations may be achieved by varying the bed volume of the filter media contained in the respective vessels, e.g., so there are vessels containing different filter media amounts therein. For flow of the water, the vessels or columns may be configured to have the same internal diameters so that the height of the pilot filter media contained therein can be different based on the height the pilot filter media occupies in a respective vessel or column. The plurality of pilot samples from the water source after contact with the pilot filter media are collected after a specified duration of time, which may be a duration where a flow volume has passed through the pilot filter media (which may be based on the hydraulic load rate of the filter media and the contaminants or other characteristics of the water source or wastewater, pH, temperature). The filter media used for the pilot is the same filter media type that will serve the full scale filter system of the water source or wastewater source that is used for the pilot samples. The supplier or manufacturer of the filter media typically desig-nates the media capacity for one or more particular con-taminants, and may provide an empty bed contact time (EBCT). The EBCT is for the media type being used, and the contaminant or contaminants to be removed from the water source or wastewater source with the filter media. One example is to determine for the filter media, a media life usage based on the contaminant concentration in the water or wastewater to be filtered. Because each water source and/or wastewater source is unique (has contaminants, as well as other substances), the filter effect may be different in terms of its effectiveness when one or more other substances are present, or other factors, such as pH levels, levels of oxygen or other compounds are present. The presence of the other substances or conditions may change the effectiveness of the filter media (from water source to water source). The flow volume allowed to pass through the filter media of each of the pilot vessels during the time period chosen for the pilot vessels and the potential contaminants in the water or wastewater source. According to some embodiments, the water or wastewater source may be spot tested for an initial contaminant level of the one or more contaminants to be filtered using the filter media of the pilot. The time that the pilot samples are taken may be based on a prediction or modeling. The modeling determines how long the filter media is expected to last, for the contaminants of interest to be removed (filtered from the water or wastewater), at the hydraulic load rate. The modeling or prediction may be based on the flow rate for the water source through the filter media used within the vessels (and the vessel sizes and hydraulic load rate), the media type and contaminants to be removed, to arrive at a time (which may be an approximate time or a range) when the sample batch is representative of the filter media utilization. A suitable model or prediction may be made using any suitable adsorption model, including for example, the Freundlich isotherm method/model. The model/method may be used to determine how much filter media to place in the one or more pilot vessels or columns. The adsorption model/method allows the pilot time to be set so that there is utilization of the filter media for the flow of water or wastewater and that the pilot filter media will be representative of effective filtration at the end time of the pilot when the samples are collected.

According to an exemplary implementation and embodiment, the breakthrough volume is generated by flowing water from the water source or wastewater source into filter media that is of the same type that will be used to filter the water source or wastewater source in the full scale filtering system. For reference, the filter media in the pilot is referred to as the pilot filter media. The pilot filter media comprises the same filter media type as the filter media that is effective to remove the one or more contaminants from the water source or wastewater source. This media type also could be a mixed media type. The breakthrough volume for the filter media and water or wastewater source is generated by collecting a plurality of samples from the water source or wastewater source. The water or wastewater that is to be filtered in a larger scale or full scale filter operation is flowed into the pilot vessels, contacts the filter media therein, and then exits the vessel. The hydraulic load rate governs the residence time and flow rate for the filter media and contaminants to be removed. During this operation, samples may be taken, which according to some embodiments may be done at one or more locations along the pilot vessel height, or according to some other embodiments may be done along an outlet of the vessel. Collecting the samples from the water or wastewater source may be carried out using the methods and apparatus described herein. A plurality of samples are collected and those plurality of samples comprise a sample batch. The batch is collected at the same time, such as for example, manually where an operator collects the plurality of samples, or where one or more automated valves are actuated to provide the plurality of samples. When an operator collects the samples manually, the operator may open a valve, and withdraw a sample into a sample container or vial. The operator may collect the samples at the same time (e.g., which typically may be serially, one after the other), and these samples collected at the same time or same day (e.g., same day site visit/pilot location), comprise the batch of samples. The automated sampling valves may be actuated together to collect samples at the same time. Preferably, the pilot sampling is done as a batch, where a single batch of samples are collected (e.g., on the same day, or during the same hour). The batch of samples are representative of the same water quality coming into the filter media of each pilot vessel or column at that point in time, of the water source or wastewater source. The plurality of samples from the water source or wastewater source include at least a plurality of samples from the water source or wastewater source after the water source or wastewater source has been in contact with the pilot filter media. The plurality of samples from the water source are taken after contact with the breakthrough or pilot filter media and comprise a batch of samples, which are samples of filtered water. In addition, or optionally, one or more samples of the water source or wastewater source can be carried out prior to any filtration to ascertain a level of one or more contaminants in the water.

For each respective sample of the batch of the plurality of samples collected from the water source or wastewater source that have been in contact with the pilot filter media, a respective concentration of the one or more contaminants present in each of the respective samples of the batch is generated. This may be done using a suitable analyzer, such as one that is designed to identify the contaminant and concentration level in the sample (such as for example, those mentioned above). Generating the concentration of the one or more contaminants present in each of the respective plurality of the samples of the batch is carried out with the contaminant analyzer which generates the concentration of the one or more contaminants in each respective sample of the plurality of samples of the batch. For each respective sample of the batch there is a concentration of the one or more contaminants that is greater than or equal to zero. For each respective sample of the batch there is a respective correspondent amount of the pilot filter media with which the water source or wastewater source from which each respective one of the plurality of samples of the batch has been in contact therewith. In other words, as shown and described herein, the pilot may be arranged with a plurality of vessels or columns from which the samples are taken. Each of the vessels of columns may be provided with a different amount or volume of filter media therein. Where the vessels or columns are of the same height, the media depth in each column may be used to associate each sample with the filter media depth. The media depth also represents a media volume, as the vessel or column diameter is known and the space the filter media takes up in the vessel or column also is known. The pilot generates a breakthrough value of the filter media volume for a flow total amount, for filtering taking place at a designated hydraulic load rate for the filter media.) The breakthrough value is the filter media amount that provides the filtered water at or lower than the designated concentration level (or levels) for the one or more contaminants. The breakthrough value also is a breakthrough value that is consistent with the designed hydraulic load rate utilized in the pilot. The pilot filter media volume may be scaled for use to generate the filter media amount for the large scale or full scale filter system that filters the water or wastewater source that the pilot has filtered and from which samples of the filtered water were taken in the pilot. According to some embodiments, the amount of filter media for the full scale or large scale filter system that effectively filters the one or more contaminants from the water source or wastewater source, and removes the one or more contaminants from the water source or wastewater source to maintain the concentration of the one or more contaminants at or lower than the designated concentration level for the one or more contaminants, for the filtered water flowing from the filtered water outlet of the filter system is the breakthrough forecasted filter media volume. The breakthrough forecasted filter media volume is for the filter media used in the pilot that also is used in the larger or full scale filter system, and is for the hydraulic load rate used in the pilot that also is used for the larger or full scale filter system. The breakthrough forecasted filter media volume is for removal of contaminants for a flow total amount of volume of the water source or wastewater source containing the one or more contaminants that flows through the filter media contained in the one or more vessels of the filter system, and which is carried out at a designed hydraulic load rate. The pilot filter media and breakthrough amount generated is used to scale the larger or full scale filter system, for the full scale filtration of the water or wastewater source using the same media type as the pilot, and flowing the water through the filter media of the larger or full scale filter system (through one or more vessels containing the filter media), and at a hydraulic load rate that the pilot used to generate the filter media breakthrough, and filter media amount to employ. The pilot breakthrough for the samples taken and their respective concentrations (of the one or more contaminants), and the flow rate that the water source or wastewater source flows through the pilot vessels or columns containing the pilot filter media, as well as the amount of the filter media in the pilot vessels, and residence time of contact that the water makes with the filter media in the pilot vessels (at or near the designed hydraulic load rate), may be scaled to treat the water or wastewater source. The hydraulic load rate (a volume of water that passes through a specific filter media surface area of a treatment unit per unit of time. e.g., gpm/ft$^2$) referenced is a range, and preferably is similar in the pilot as it is in the full or larger scale filter system. The full scale filter media amount is the breakthrough forecasted filter media amount from the plurality of pilot samples for the designated concentration level of the one or more contaminants, and for the designed hydraulic load rate.

According to some embodiments, the breakthrough forecasted filter media amount from the plurality of samples for the designated concentration level of the one or more contaminants in may be measured in bed volumes, and the filter media amount may be the forecasted bed volume of media that maintains the concentration of the one or more contaminants at or lower than the designated concentration level for the one or more contaminants, for filtered water flowing from the filtered water outlet. According to some other embodiments, the breakthrough forecasted filter media amount from the plurality of samples for the designated concentration level of the one or more contaminants may be measured in bed volumes, and the filter media amount is the forecasted depth of the filter media that maintains the concentration of the one or more contaminants at or lower than the designated concentration level for the one or more contaminants, for filtered water flowing from the filtered water outlet.

The system may be provided as an electronically actuated method. For example, the electronically actuated implementation can comprise actuating a controller to provide the breakthrough forecast, and the breakthrough forecasted filter media amount for the filter media from the concentration of contaminants for each respective sample of the batch and the respective pilot filter media volume for each sample of the batch, wherein the breakthrough forecasted filter media amount for the filter media comprises the filter media amount in the vessels of the filter system.

According to embodiments, the filter media amount used in the filter system may be distributed among the one or more vessels in communication with the contaminated water or wastewater inlet and the filtered water outlet.

The vessels or columns of the pilot may contain the pilot filter media, and preferably, at least some of, or each of, the pilot vessels or columns contain different amounts of the pilot filter media. The respective contaminant concentration is generated for each of the respective pilot samples, and the breakthrough may be generated by correlating depths and concentration of contaminants, and forecasting the anticipated media life for the water source or wastewater source that the filter system is employed to remove contaminants from.

The breakthrough forecasted filter media amount is an amount of filter media from a forecasted volume of filter media from the concentration of the one or more contaminants of each respective pilot sample of the batch versus the pilot filter media amount contained in each respective ones of the pilot vessels. So that for each sample, and its respective contaminant concentration level (of one or more contaminants), there is a respectively associated pilot filter media amount, which may be a bed volume of pilot filter media. In some implementations, the pilot filter media volume is referred to as the bed height. The generation of the filter media volume for the filter system may be from the pilot forecasted breakthrough volume, and in the exemplary depictions is shown generated without an actual breakthrough of the pilot filter media. The filter media may be a single filter media type, or may be a filter media of a plurality of filter types (where the pilot filter media would be the same filter type or types for the large scale filter system). The pilot filter vessels may contain a single filter type, or may contain a plurality of filter types (where the full scale filter system will use the same arrangements).

Collecting the pilot samples may carried out by actuating a valve provided for each sample location on each one of the respective plurality of vessels. As shown and described herein, the exemplary vessels and columns are depicted with sampling capabilities, which may include valves on the vessel or columns or associated therewith to regulate a flow of water from the column or vessel at a desired sampling location. Collecting the plurality of samples from the water source or wastewater source pilot vessels may be carried out manually by opening a flow control valve to admit flow from a sample port of the vessel into a sample vial. Alternatively, collecting the plurality of pilot samples from the water source or wastewater source pilot vessels may be carried out via automated flow control valves actuated based on the timer or an operator signal, to open a respective plurality of flow control valves to admit flow from respective sample ports of the respective vessels into a respective sample vial, wherein each automated flow control valve is associated with a respective one of the sample ports of each vessel.

The system may employ a suitable filter media and types of media for removal of the designated contaminant or contaminants from the water source or wastewater. One example of a filter media type comprises granular activated charcoal (GAC). Another example of a filter media type comprises an ion exchange filter media. Alternatively, the filter media may comprise a mixed filter media, including a first type of filter media, and a second type of filter media. For example according to some implementations, at least one of the first type of filter media may comprise granular activated charcoal (GAC), and there may be a second type of media comprising a different filter media type. As an example, a first type of filter media may comprise granular activated charcoal (GAC), and a second type of filter media may comprise ion exchange filter media.

A filter effective to filter one or more contaminants from a water source or wastewater source is provided that includes an inlet, an outlet, and contains one or more vessels between the inlet and outlet in clow communication therewith. The filter includes a media space therein and filter media, where the filter media comprises a volume of filter media generated from a pilot where a plurality of samples of the contaminant-containing water are filtered, and where the samples contaminant concentrations and associated pilot filter media of each associated sample vessel are used for the breakthrough forecast. The breakthrough forecast of the pilot generates the filter media amount for the filter that is effective to filter one or more contaminants from a water source or wastewater source. The samples are a batch of samples taken at a time (as discussed herein). The filter media amount for the filter system or filter employs an amount of the filter media from the flow total amount for the pilot that will filter contaminants, and employs the one or more vessels (and their volumes, e.g., height and/or diameters) for the filter to operate at the designed hydraulic load rate that the pilot operated to provide the breakthrough amount.

Detailed Description of a PFAS Roughing Filter Method and Apparatus

A traditional design for pressure vessels used to treat water for PFAS is a pair of vessels in series. This treatment arrangement is referred to as a lead-lag setup. As soon as breakthrough of PFAS occurs in the first vessel (the lead vessel) measured at a point between the pair of vessels, the system is considered to be due for a media changeout. At which point the media in the lead vessel is replaced, and valves are used to reverse the flow though the vessel pair to make the prior lag vessel the new lead vessel. This process is repeated in perpetuity. For additional treatment capacity pairs of lead-lag vessels are installed in parallel. Optionally, instead of swapping lead and lag vessels during a media changcout, some users may replace both vessel's media for logistical simplicity.

According to another aspect of the invention, the invention is implemented by providing and maintaining a series configuration of pressure vessels, but instead does not rely solely on a pair of lead-lag vessels. Instead, the invention does not prescribe a certain number of pressure vessels in series, it only recommends more than two vessels in series in what will now be referred to as a treatment train. Then for additional treatment capacity, parallel treatment trains can be employed. The reason for the additional vessels is to completely exhaust the upstream vessels, the roughing filters, prior to the final vessel of the treatment train. In a traditional approach when breakthrough of the lead vessel occurs, the tank is swapped prior to completely exhausting the adsorptive capacity of the media. This must be done to avoid breakthrough occurring in the lag vessel resulting in a compliance violation. The extra filters, the roughing filters, of the treatment train allow for complete exhaustion of the media without risking breakthrough of the final vessel of the train which would result in a compliance violation. In other words, the roughing filter approach allows for the recovery of adsorptive capacity otherwise lost in traditional treatment methods. The invention promotes conservation by maximizing the utilization efficacy and capacity of the filter media. This has important environmental benefits as well as economic benefits.

The pressure vessel roughing filter method can be employed for greenfield or brownfield applications. For brownfield applications additional vessels can be installed upstream or downstream of existing vessels. When installed upstream of the existing vessels, the new vessels and the original lead vessel are the roughing filters. When installed downstream of existing vessels, the existing vessels become the treatment train's roughing filters as do the new vessels up to the last lag vessel. The roughing filter method can be employed using a variety of media types, and it can be employed with or without other forms of pretreatment.

Embodiments and implementations of the apparatus and methods according to the invention are illustrated in the exemplary depictions in FIGS. 13 and 17-27. Referring to FIGS. 13 and 17-25, a single media type is being used throughout a series connected treatment train at both full scale and pilot scale. However, mixed media types may be employed in those series connected vessels at full scale and pilot scale while retaining the same principle for the roughing filters of using upstream vessels to exhaustion as shown in the exemplary depictions of FIGS. 26 and 27.

Pressure Vessel Roughing Filter Pilot Testing

When pressure vessel roughing filters are to be employed, they can be designed by traditional water treatment process modeling techniques. However, since modeling can often be complicated and carry risks of inaccuracies, pilot studies can be an attractive design tool to determine the number of vessels, size of vessels, maintain Empty Bed Contact Time (EBCT), ensure proper media loading rates, and determine rates of roughing filter exhaustion. With pressure vessel roughing filters, the pronounced media utilization and extended media life would mean a pilot study would become even more expensive and time consuming when using traditional pilot approaches. The batch pilot method of the invention allows for the effective testing of pressure vessel roughing filters without bearing the additional cost and time consumption of traditional pilot approaches.

FIGS. 12 and 14-16 are diagrams and schematic illustrations relating to prior art methods. FIGS. 13 and 17-27 illustrate embodiments and implementations according to the invention. The figures (FIGS. 13 and 17-27) do not differentiate between the traditional pilot method, RSSCT, or the batch method of the invention since the roughing filter can be tested using any of the three approaches. However, as mentioned above, the batch pilot method of the invention carries significant advantages over traditional and RSSCT pilot methods due to the extended timeframe of the pilots for pressure vessel roughing filter design.

Figure 12:
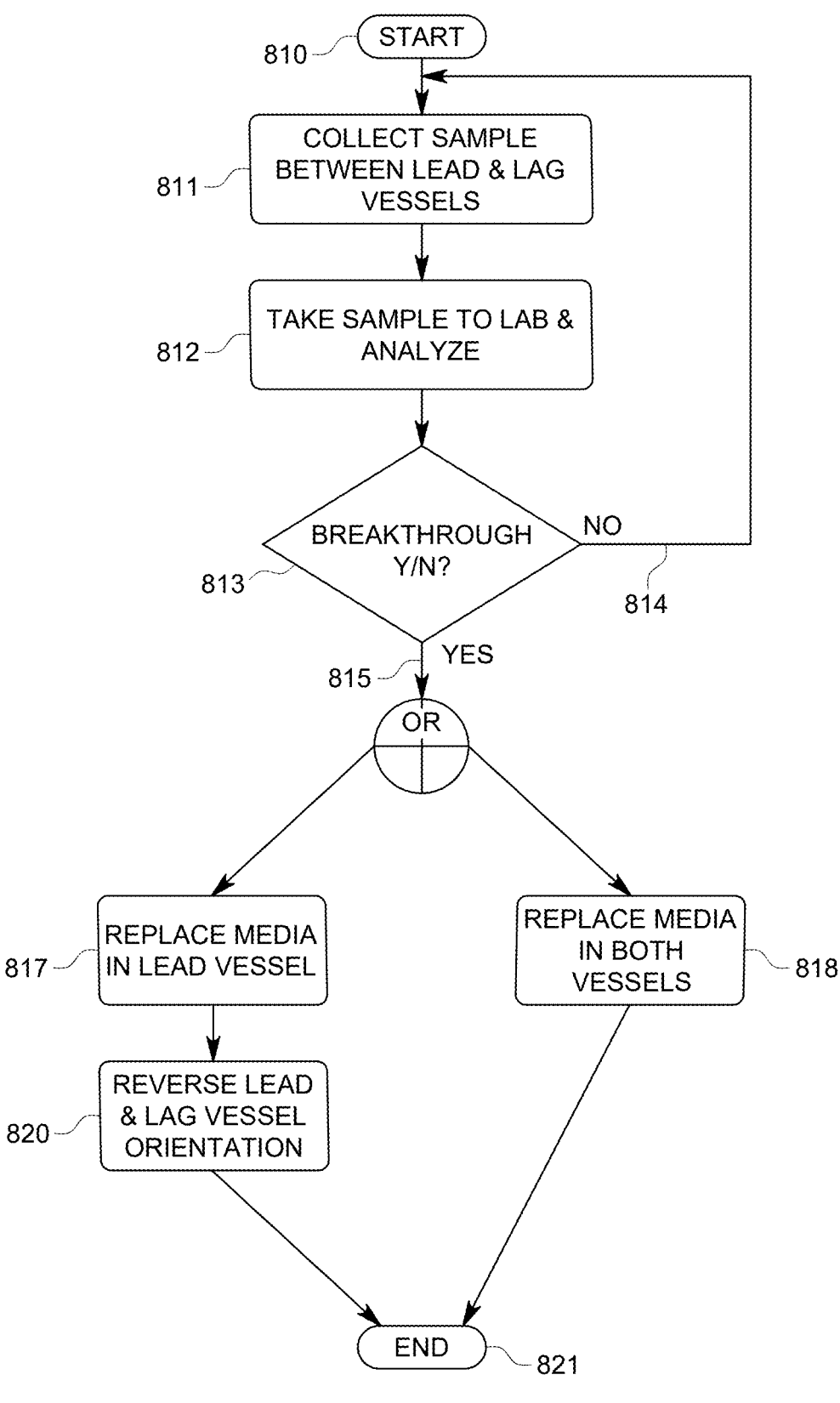
FIG. 12 is a flow diagram depicting an existing process for traditional PFAS lead-lag pressure vessels (prior art).

Referring to FIG. 12, a flow diagram is shown depicting an existing process for a traditional lead-lag PFAS treatment configuration. The process entails running two pressure vessels in series and collecting water quality samples between the two vessels. When PFAS is detected between the two vessels, a media changeout of either the lead vessel or optionally both vessels is triggered. If a media changeout is conducted for the lead vessel only, the orientation of the vessels is reversed to make the former lag vessel the new lead vessel. The reversal of the vessel orientation is done to prevent accidentally sending any PFAS that made its way into the lag vessel from propagating into the distribution system and creating a compliance violation. In FIG. 12, the traditional process is depicted showing the start 810 of the process, where a sample is collected between lead and lag vessels 811. Next the sample is taken from the sampling location to a lab for analysis 812. The analysis determines whether there is breakthrough of the filter media 813. If there is no breakthrough 814, then the process steps are repeated, including collecting the sample 811, taking the sample to the lab for analysis 812 and determining whether and when there is a breakthrough 813. If a breakthrough is determined 815, then there are options implemented one option 817 is to replace the filter media in the lead vessel. Another option is to replace the media in both vessels, 818 in this traditional process, the replacement of media in the lead vessel 817 is followed by a step of reversing the lead and lag vessel orientation 820 so that the former lead vessel now becomes the lag vessel and vice versa. The process then terminates 821.

Figure 13:
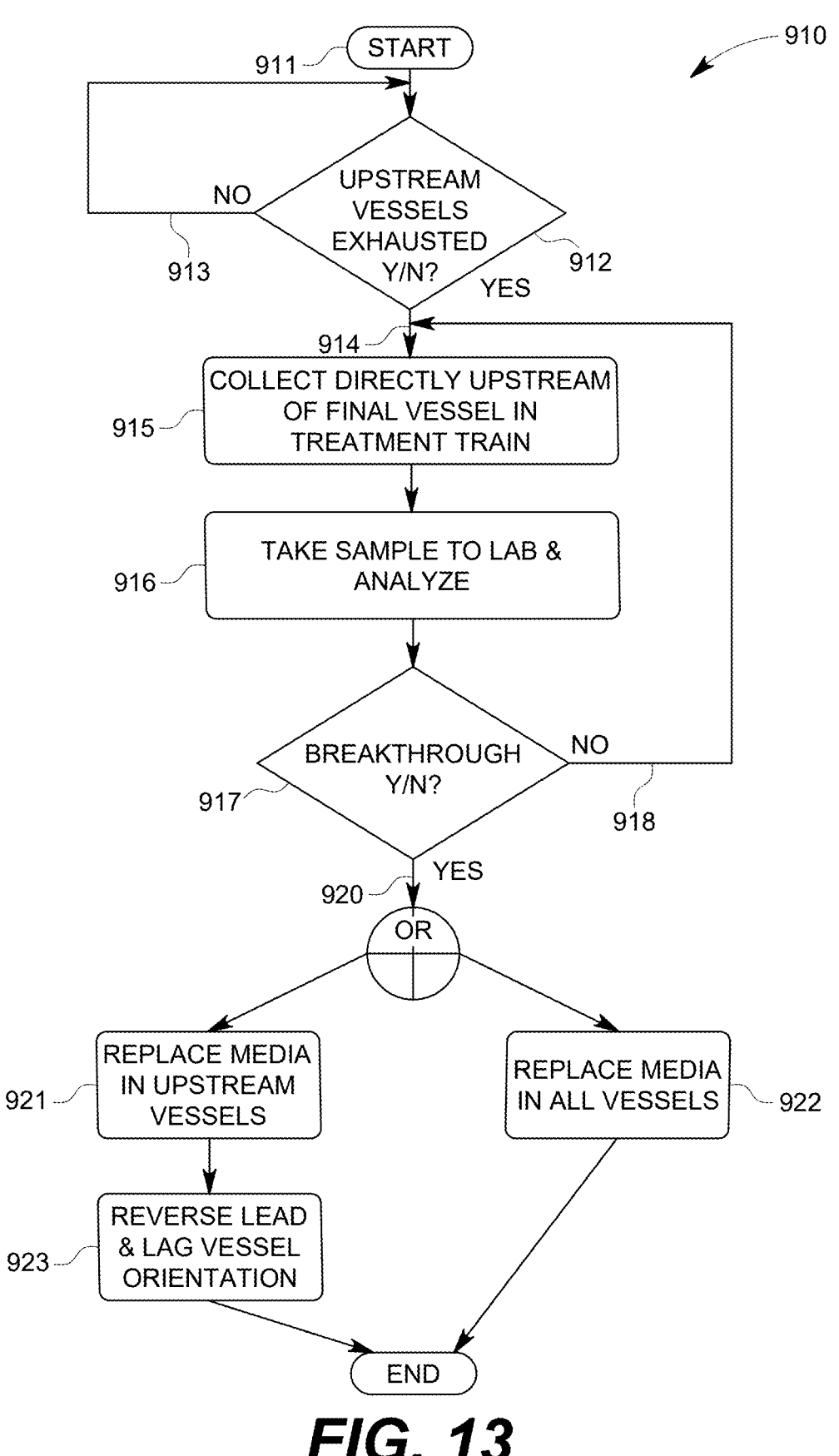
FIG. 13 is a flow diagram depicting an exemplary embodiment of a process according to the invention for pressure vessel roughing filter implementation.

Referring to FIG. 13, a flow diagram is shown depicting an exemplary process according to an implementation and embodiment of the invention where the additional pressure vessels (which are the roughing pressure vessels) upstream of the final pressure vessel are employed. Until the media in the roughing pressure vessels is exhausted, a media changeout is not required. However, if PFAS is detected entering the final vessel, a media changeout is triggered. Then media changeouts are conducted much like the existing process. In FIG. 13, an exemplary depiction of a method according to the invention is shown in the process flow diagram. The process 910 starts 911 and there is a determination whether the upstream vessels are exhausted 912. If the upstream vessels are not exhausted. 913 then the determination is made to continue to monitor the upstream vessels for exhaustion. If the upstream vessels are determined to be exhausted, 914, then a sample is collected directly upstream of the final vessel in the treatment train 915 sample or samples are analyzed, which, for example may involve taking the sample to a laboratory for analysis. Although it is possible in some instances to conduct an analysis on site or where the sample is taken, generally certified laboratories are required to conduct the analysis in most instances. Based on the laboratory analysis of the sample, there is a determination of whether there is a breakthrough 917. If there is no breakthrough 918 then the process continues with the collection directly upstream of the final vessel in the treatment train 915, the sample analysis 916 and breakthrough determination evaluation 917. If there is a breakthrough that is determined 920, then there are options implemented. One option 921 is to replace the filter media in the upstream vessels 921. Another option is to replace the media in all of the vessels, 922. Where the media is replaced in all of the upstream vessels, then the treatment train orientation is reversed 923, so that the former final vessel in the treatment train now becomes the first vessel in the treatment train, and the former first vessel in the treatment train becomes the final vessel in the treatment train.

Figure 14:
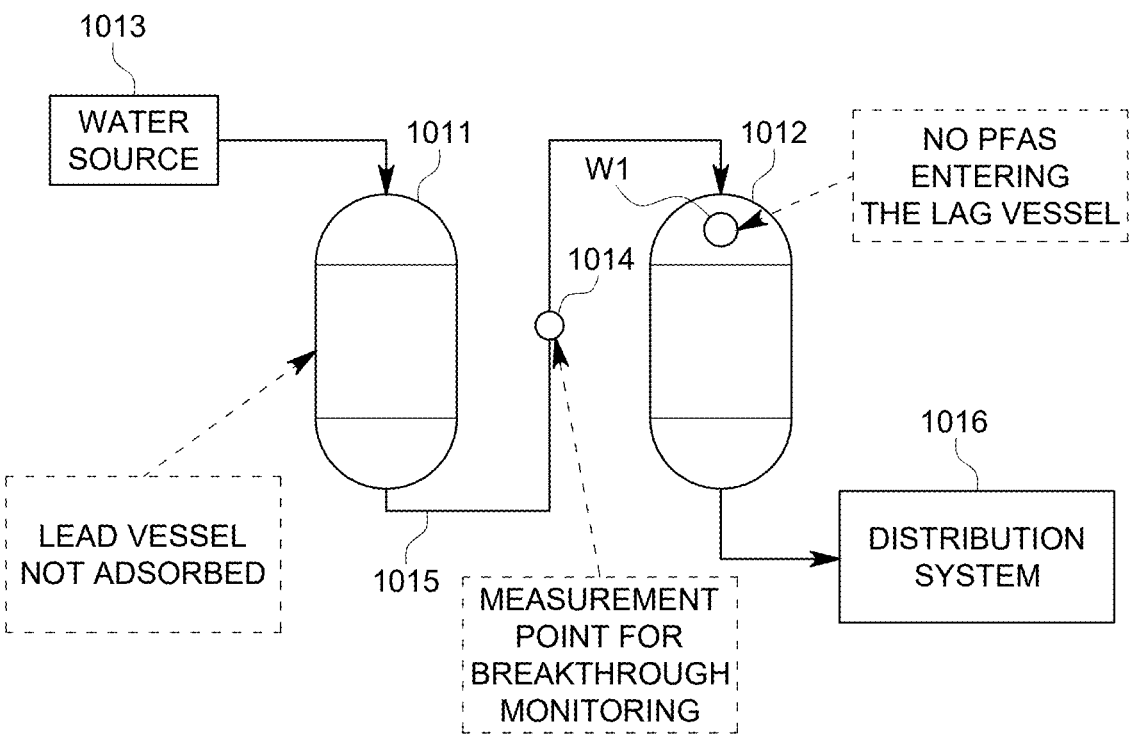
FIG. 14 is a flow diagram depicting an existing process for traditional PFAS pressure vessels at the time of system startup (prior art).
Figure 15:
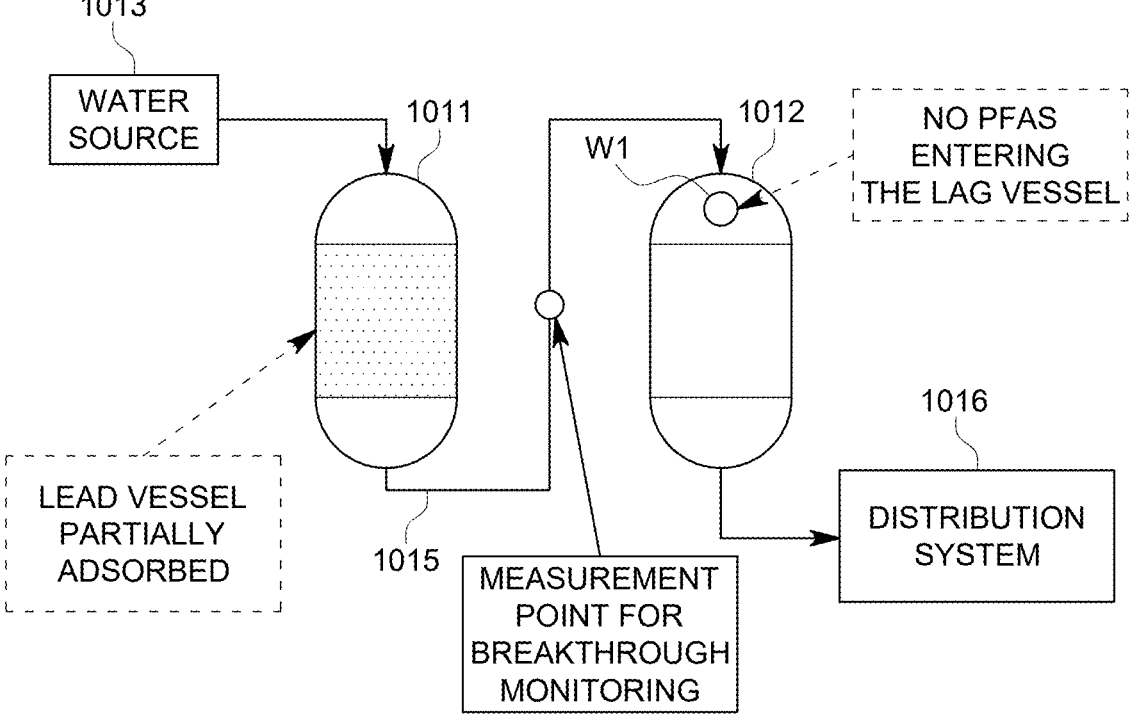
FIG. 15 is a flow diagram depicting an existing process for traditional PFAS pressure vessels at the time after system startup (prior art).
Figure 16:
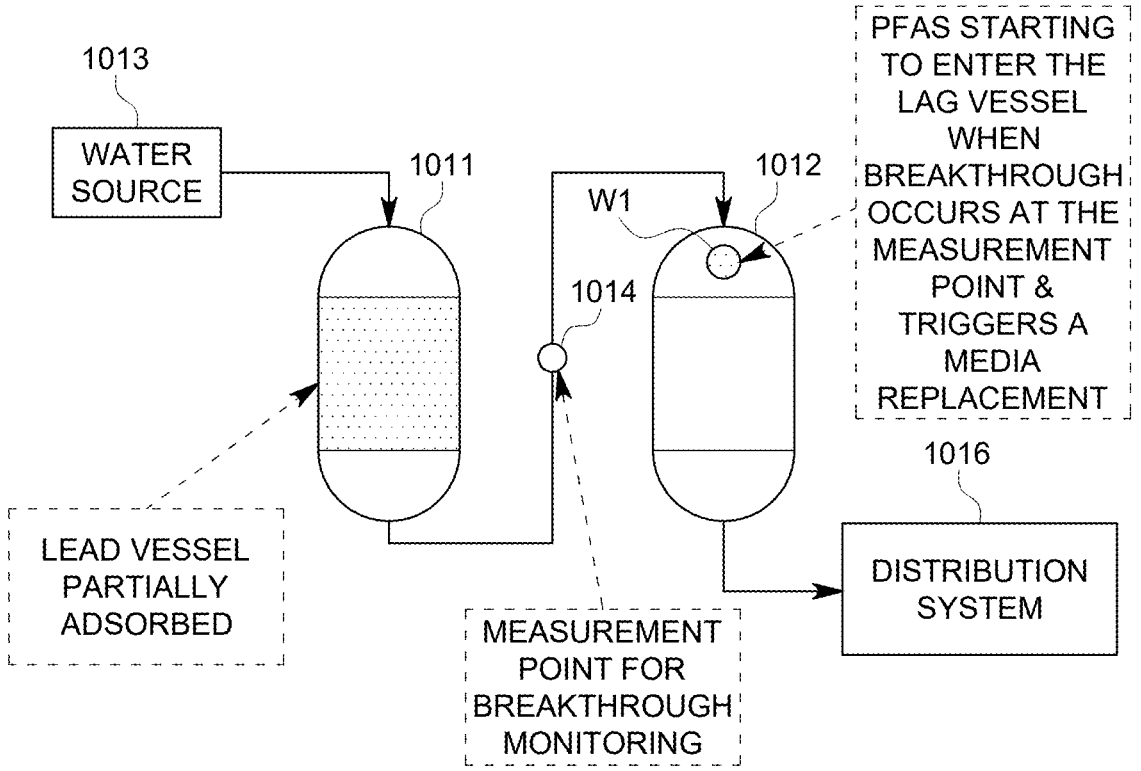
FIG. 16 is a flow diagram depicting an existing process for traditional PFAS pressure vessels at the time after PFAS breakthrough (prior art).

Referring to FIG. 14, and existing process is shown for traditional PFAS in pressure vessels at the time of system start up. A first pressure vessel 1011 is shown with a second pressure vessel 1012. In this figure, the water source 1013 is shown entering the first pressure vessel 1011, which is the lead vessel, and the measurement point 1014 being located in a connection 1015 between the first vessel 1011 and the second vessel 1012. The measurement point 1014 is a location between the first and second vessels 1011, 1012 where the breakthrough is monitored. The output from the second vessel 1012 flows to the distribution system 1016. Referring to FIG. 14 the depiction shows when the lead vessel 1011 has filter media that is fresh or not adsorbed. The second vessel 1012 is shown with a window W1 for illustration purposes representing the condition of no PFAS entering the lag vessel 1012. Referring to FIG. 15 the first vessel 1011 is shown depicted in a condition where the lead vessel filter media is partially adsorbed. Referring to FIG. 16, the depiction of the pressure vessels is at a time after PFAS breakthrough and shows the PFAS starting to enter the lag vessel 1012 when breakthrough occurs at the measurement 1014, and triggers a media replacement. The window W1, shown for illustration purposes only, represents a condition of PFAS starting to enter the lag vessel 1012.

Figure 17:
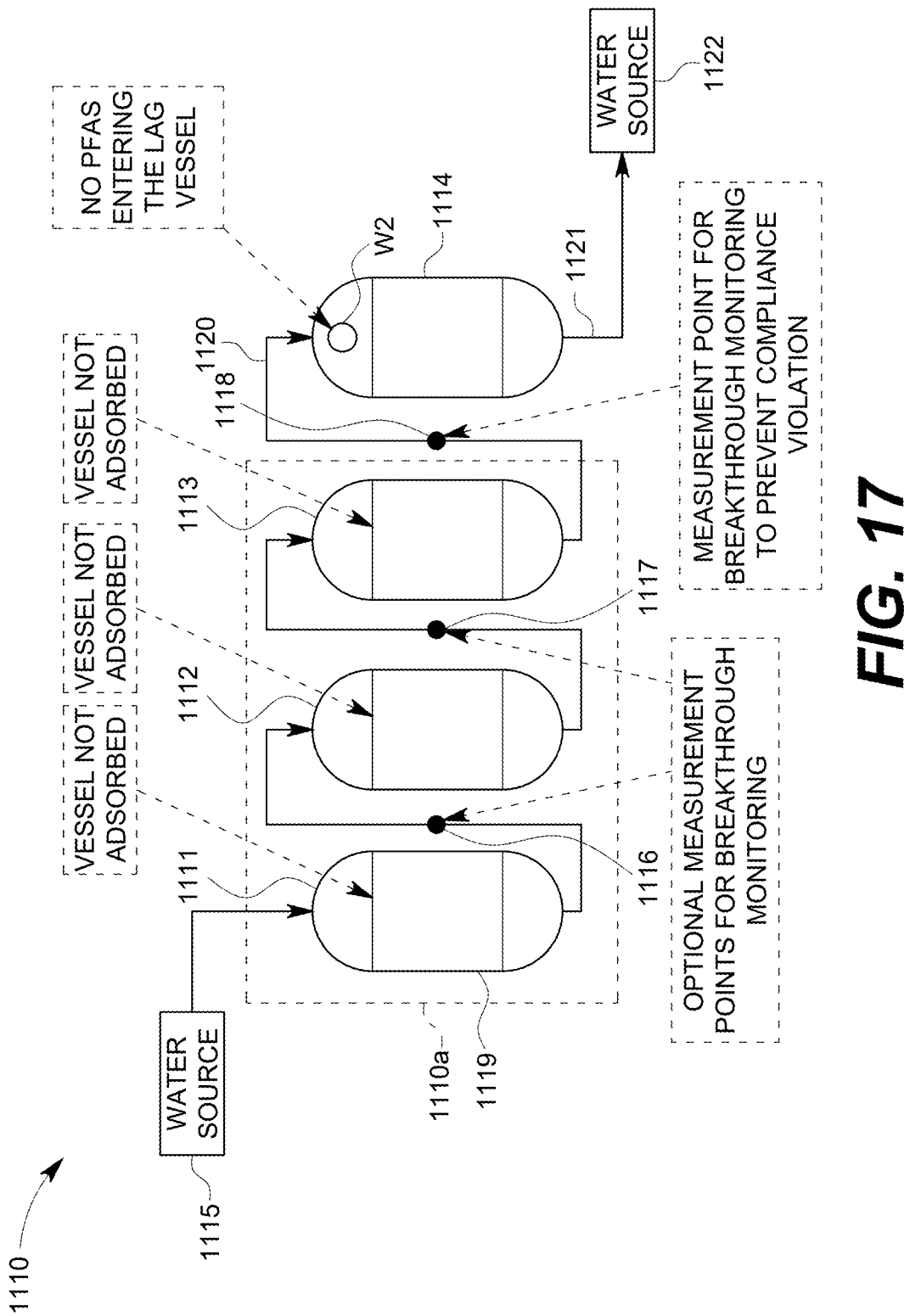
FIG. 17 is a process flow diagram for pressure vessel roughing filter at the time of system startup, according to an implementation of the invention.

FIG. 17 is a process flow diagram, showing a system 1110 with a pressure roughing filter 1110a at the time of system start up according to an embodiment and implementation of the invention. The roughing filter 1110a is shown according to an exemplary embodiment having three pressure vessels, although different numbers of pressure vessels may make up the roughing filter. In the illustration of FIG. 17, there is shown an example pressure vessel roughing filter arrangement 1110 with three roughing filters, 1111, 1112, 1113 and the final main filter 1114 post media replacement or system startup and all vessels are unadsorbed. A water source 1115 is shown feeding into the first roughing filter vessel 1111. A plurality of monitoring points are shown 1116, 1117, 1118. The first monitoring point 1116 is shown between the first roughing filter vessel 1111 and the second roughing filter vessel 1112. A second monitoring point 1117 is shown between the second roughing filter vessel 1112 and the third roughing filter vessel 1113 and the third roughing filter vessel 1113. A monitoring point 1118 is shown between the last vessel of the roughing filter vessels, 1113 in this example of which there are three roughing filter vessels. The monitoring point 1118 is between the last roughing filter vessel 1113 and the final 1114 or main filter. The third monitoring point 1118 located between the roughing filter and the main vessel 1114. In the arrangement of the system 1110 shown in FIG. 17, the final vessel 1114 receives an inflow 1120 from the last roughing filter vessel, which in the exemplary embodiment is the vessel 1113. The outflow 1121 from the final vessel 1114 is supplied for distribution 1122 to an intended source, for further processing and/or distribution to a water system. In the depiction in FIG. 17, the system is depicted at the startup time, so the filter media, including the first roughing vessel 1111 and its associated media 1119, have not adsorbed PFAS (assuming the filter media 1119 is unused/fresh/new filter media). There is no prescribed number of roughing filters other than creating a total number of vessels per train greater than the two traditional lead-lag vessels. The monitoring points 1116, 1117 may be optionally provided, but if provided, provide options for monitoring between vessels of the roughing filter, 1110 a. Although schematically represented, the connections shown between the vessels may comprise piping or other suitable connections. In addition, one or more valves may be provided to regulate flow to any one or more of the roughing filter vessels, and/or main vessels, for installation and/or removal or reorientation of one or more of the pressure vessels. The sampling points, such as those 1116, 1117, 1118 may comprise a suitable valve or port, and may connect with any sample collection container. This may be manual such as a manual valve, or may be electronically operable using an electronic valve. The sample collection methods and apparatus disclosed herein in connection with other embodiments and implementations, may be used in conjunction with sampling of the system 1110 shown in FIG. 17.

Figure 18:
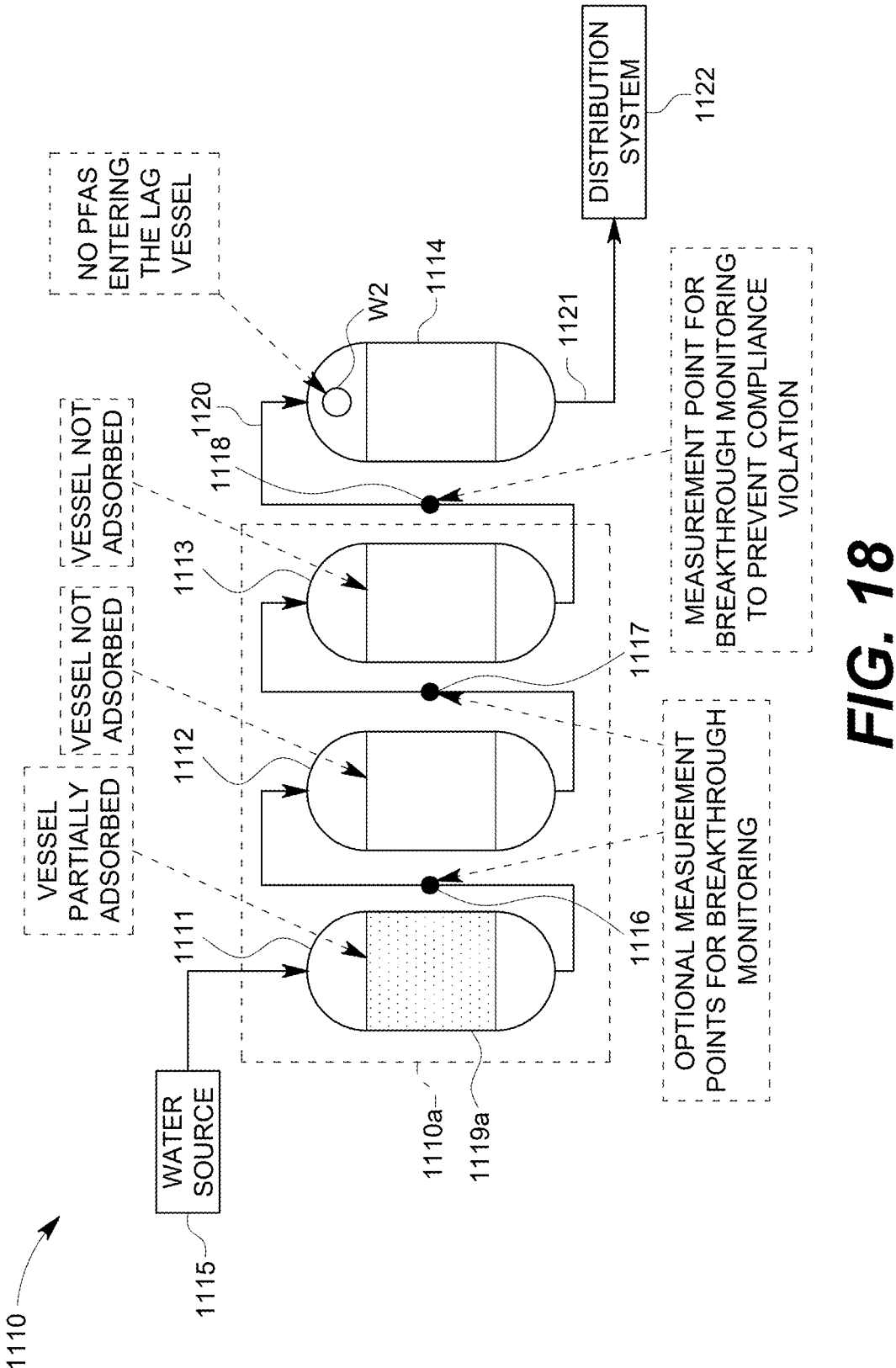
FIG. 18 is a process flow diagram for pressure vessel roughing filter with first vessel adsorbing, according to an implementation of the invention.

Referring to FIG. 18, the system 1110 of FIG. 17 is shown, as an example pressure vessel roughing filter arrangement 1110a, but after some time has elapsed post media replacement or system startup. In this case, the first vessel of the treatment train is adsorbing both PFAS and competing water quality parameters. In this case breakthrough to the second vessel of the treatment train has not yet occurred. However, in contrast to the filter media 1119 in FIG. 17, the filter media 1119a in FIG. 18 begins adsorbing. At the last or lag vessel 1114, the illustration window W2 as it appears in FIG. 18, indicates no PFAS entering the vessel.

Figure 19:
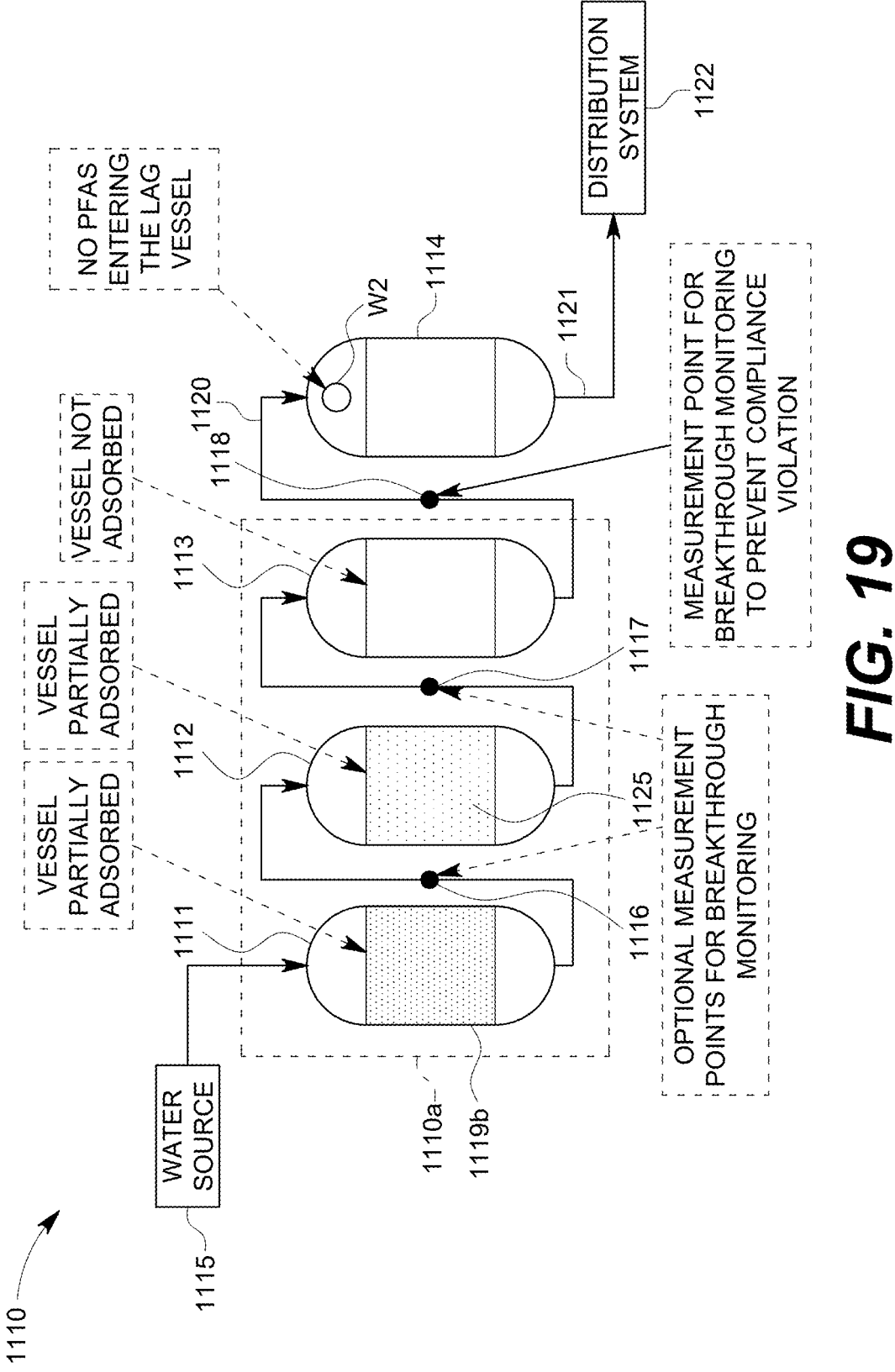
FIG. 19 is a process flow diagram for pressure vessel roughing filter with second vessel adsorbing, according to an implementation of the invention.

As shown in FIG. 19, the roughing filter 1110a is shown further along in a process of filtration that the representation in FIG. 18. In FIG. 19, the filter media 1119a continues adsorbing, and the filter media 1125 of the second vessel 1112 in the series of the roughing filter 1110a began adsorbing. FIG. 19 shows the example pressure vessel roughing filter arrangement 1110a after some time has elapsed post media replacement or system startup (see FIG. 17). In FIG. 19, in the exemplary state of adsorption depicted, the first vessel 1111 of the treatment train is adsorbing both PFAS and competing water quality parameters, and the first vessel 1111 has progressed into a state of more complete exhaustion compared to FIG. 18. Also, in this state shown in FIG. 19, breakthrough to the second vessel 1112 of the treatment train has occurred, and now the first vessel 1111 is left in operation to reduce the load of both PFAS and competing parameters on the second vessel 1112.

Figure 20:
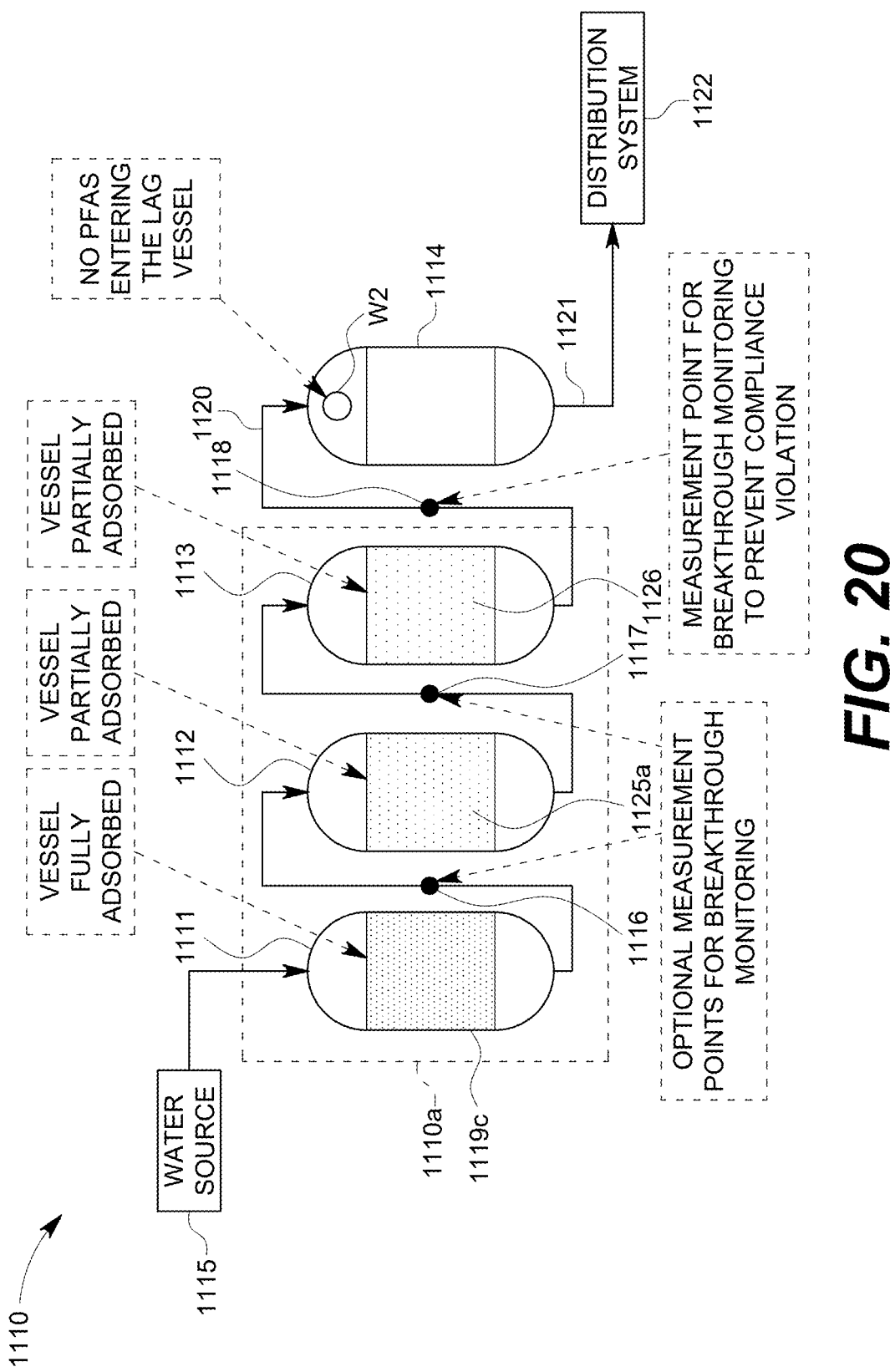
FIG. 20 is a process flow diagram for pressure vessel roughing filter with third vessel adsorbing, according to an implementation of the invention.

Referring to FIG. 20, an example of the pressure vessel roughing filter arrangement 1110a is depicted in a state after some time has elapsed post media replacement or post system startup. In this case, the first and second vessels 1111,

1112, respectively, of the treatment train are adsorbing both PFAS and competing water quality parameters, and both vessels have progressed into a state of more complete exhaustion compared to FIG. 19 (see e.g., 1119$c$ and 1125$a$). Also, in the case represented in FIG. 20, breakthrough to the third vessel 1113 of the treatment train has occurred, and now the upstream vessels are left in operation to reduce the load of both PFAS and competing parameters on the third vessel.

Figure 21:
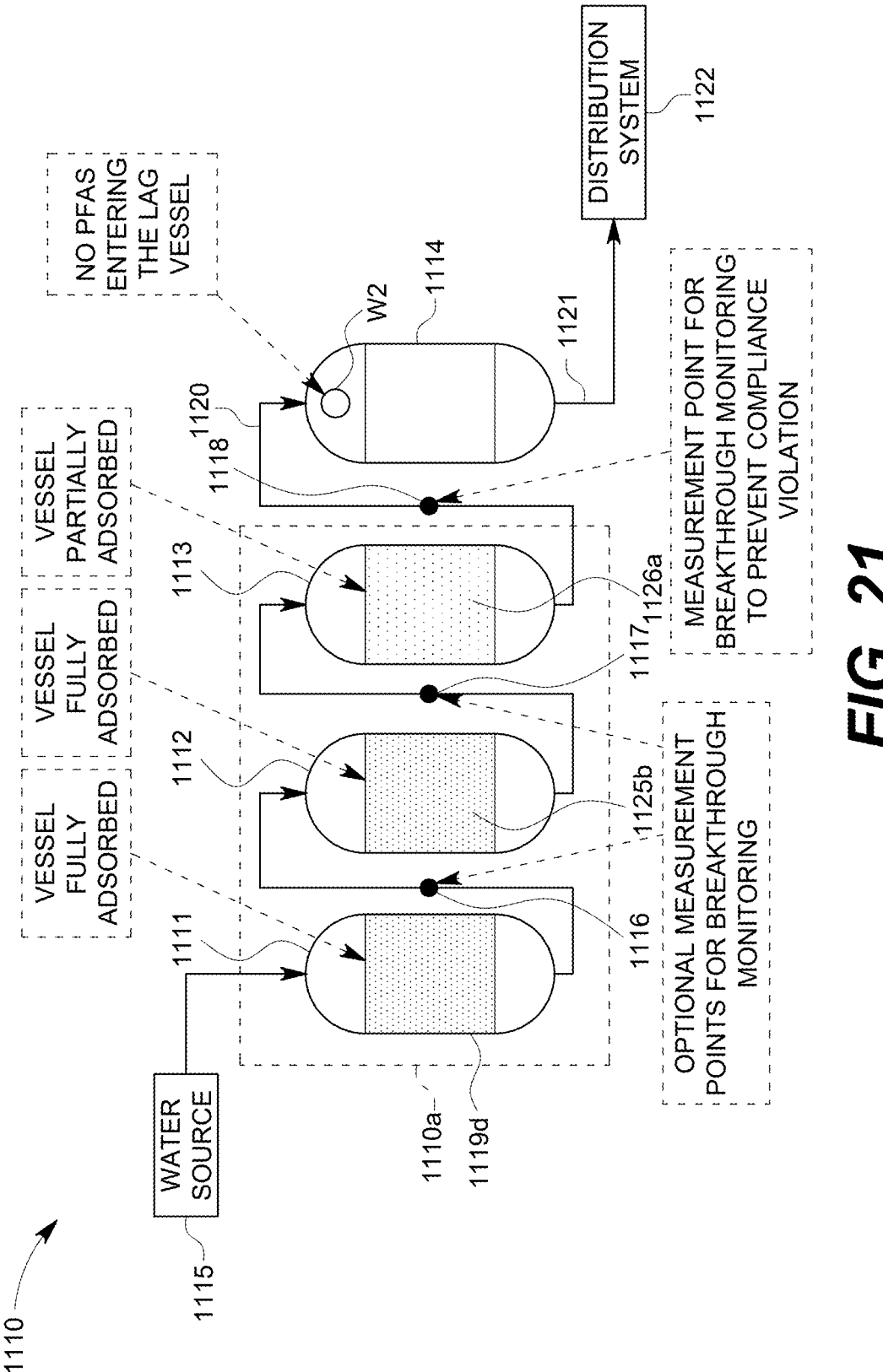
FIG. 21 is a process flow diagram for pressure vessel roughing filter with upstream vessels fully utilized according to an implementation of the invention.

Referring to FIG. 21, an example of the pressure vessel roughing filter arrangement 1110$a$ is depicted in a state after more time has elapsed compared to FIG. 20. In this case, the first and second vessels 1111, 1112 of the treatment train have continued to adsorb both PFAS and competing water quality parameters, and both vessels have progressed into a state of more complete exhaustion compared to FIG. 20. Also, in this case, breakthrough to the final vessel 1114 of the treatment train has not occurred, and the upstream vessels are left in operation to reduce the load of both PFAS and competing parameters on the third vessel. In FIG. 21, the filter media 1119$d$ of the first vessel 1111 and filter media 1125$b$ are each shown being in a state or condition of full adsorption, while the third vessel 1113 of the roughing filter 1110$a$ is shown in a condition of partial adsorption.

Figure 22:
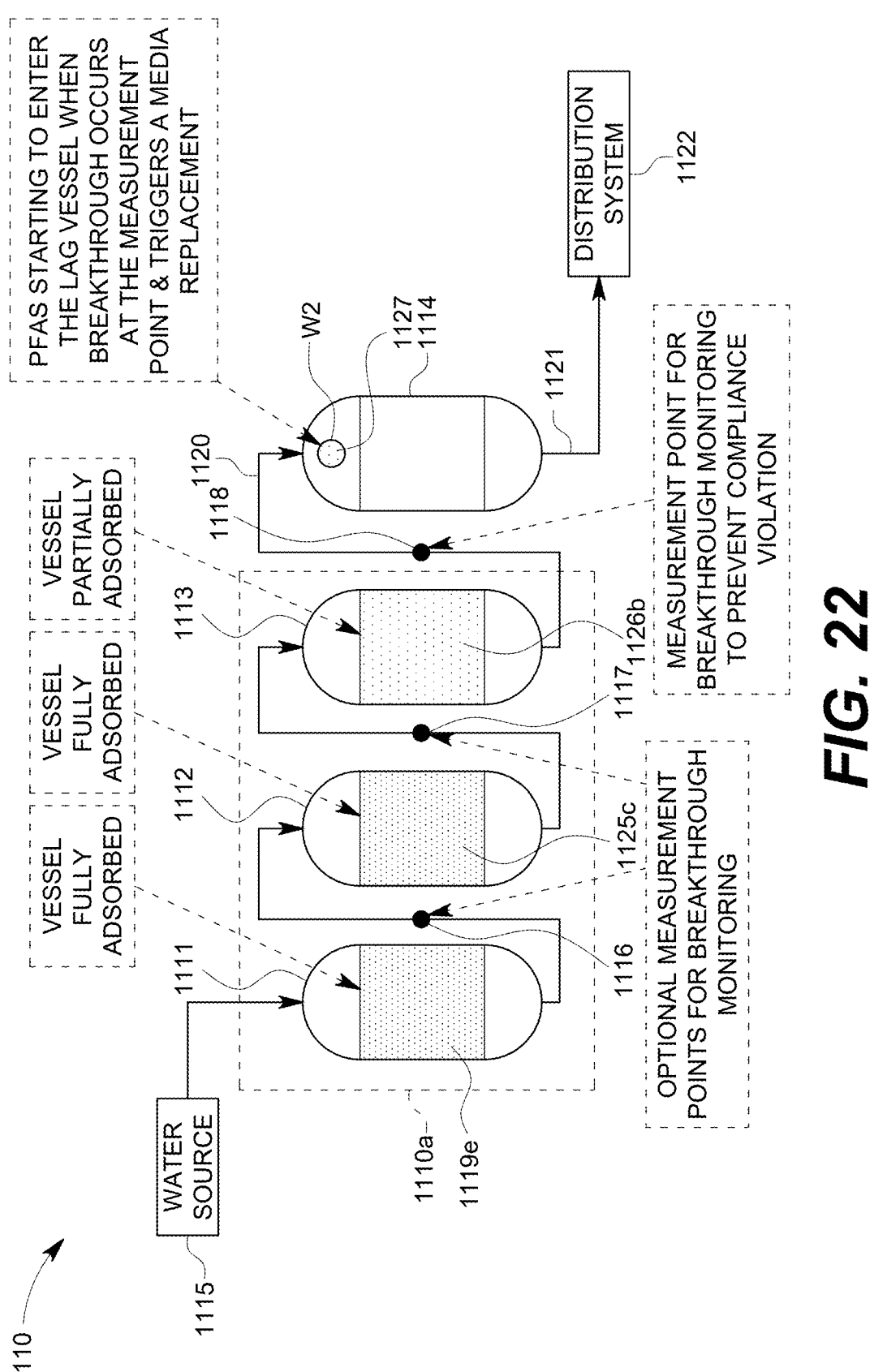
FIG. 22 is a process flow diagram for pressure vessel roughing filter at the time after PFAS breakthrough, according to an implementation of the invention.

FIG. 22 is similar to FIG. 21, except that more time has elapsed compared to FIG. 21. In this case, the first and second vessels 1111, 1112 of the treatment train have continued to adsorb both PFAS and competing water quality parameters, and both vessels have progressed into a state of near complete exhaustion compared to FIG. 21 (see FIGS. 22, 1119$e$ and 1125$c$). Also, in this case, breakthrough to the filter media 1127 of the final vessel 1114 of the treatment train has occurred which triggers a media replacement action (see the cutaway view W2 for illustration purposes only, where, in FIG. 22, the PFAS is starting to enter the lag vessel 1114 and is represented by the media 1127).

Figure 23:
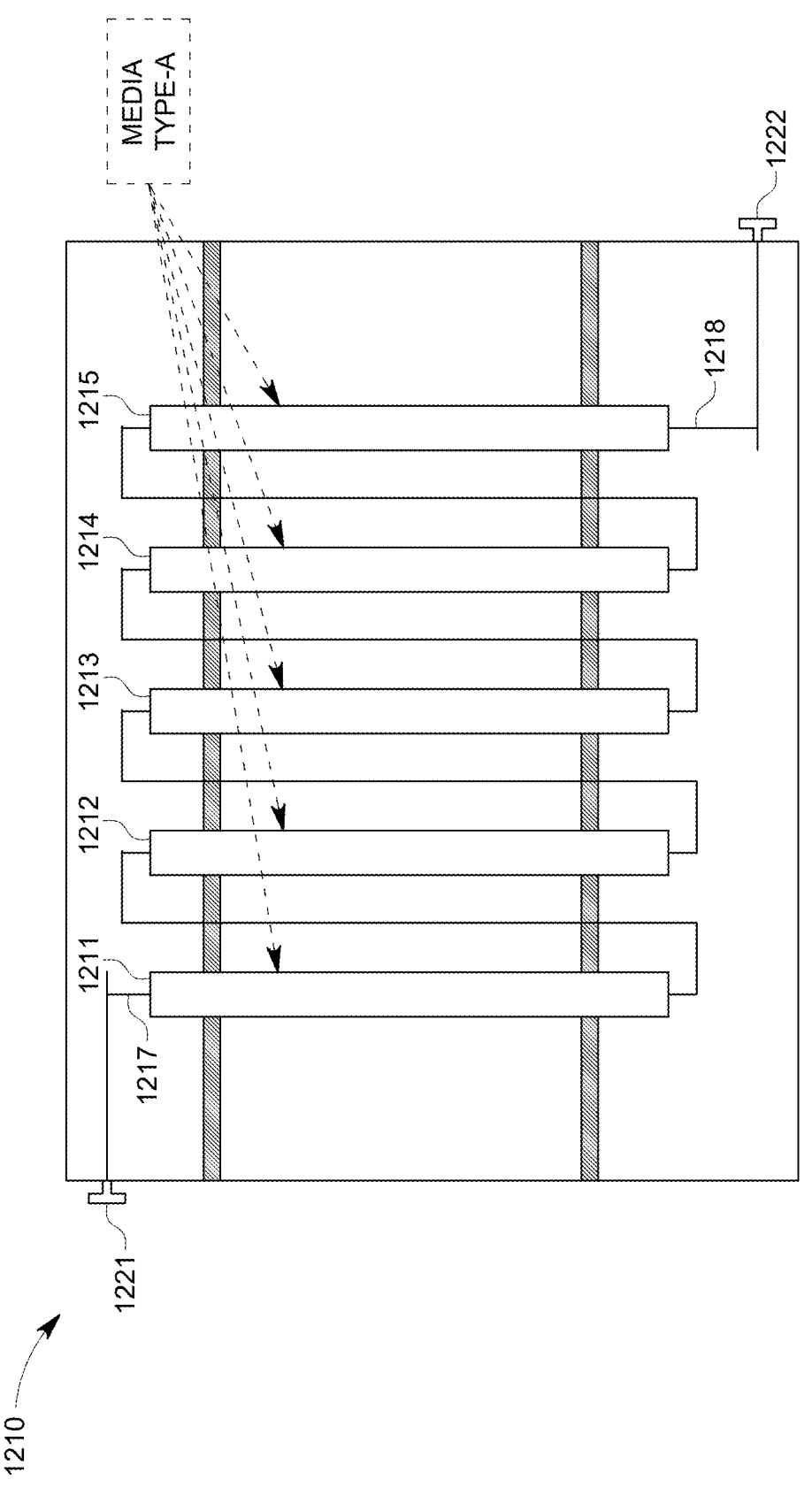
FIG. 23 is a schematic illustration showing a front elevation view of a pressure vessel roughing filter pilot example for single skid, according to an exemplary embodiment of the invention.
Figure 24:
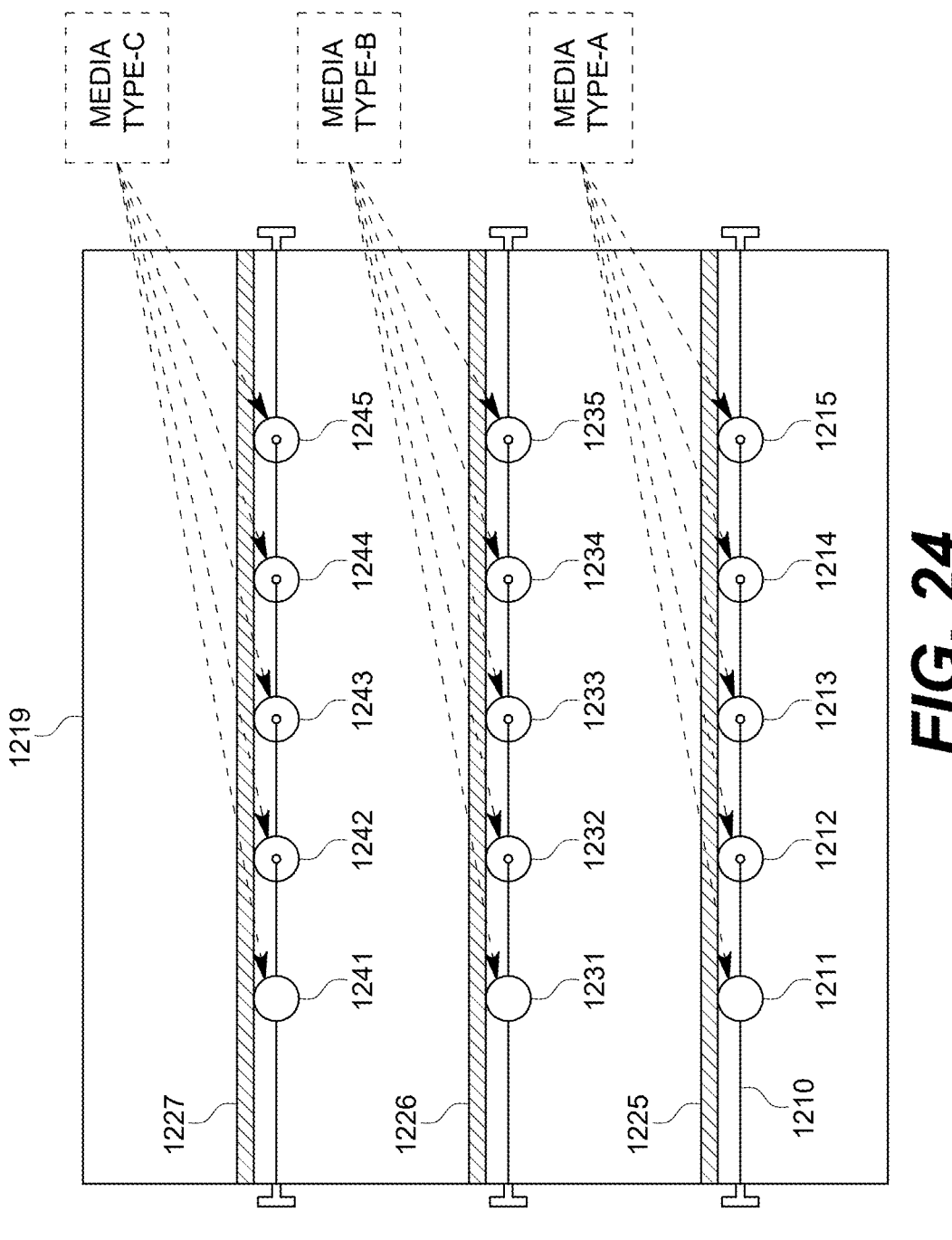
FIG. 24 is a top plan view of the pressure vessel roughing filter pilot example for single skid shown in FIG. 23.

FIG. 23 shows an exemplary implementation of a pilot method and system 1210 according to the invention for a pressure vessel roughing filter configuration where the pilot tubes of the same media are all connected in series within a pilot skid. A plurality of tubes 1211, 1213, 1214, 1215 are shown connected in a series, and including a water inlet 1217 and water outlet 1218. An inlet valve 1221 and outlet valve 1222 are shown. There may be additional valves between or along the fluid connections between the vessels that allow for sampling or exchanges of the tubes. FIG. 24 shows the system 1210 of FIG. 23 in a top plan view, along with other arrangements of pilot tubes for two additional media types, Media B. and Media C. The exemplary implementation shows an example where three media types, A, B and C are depicted in parallel for a pilot test. The first unit 1225 involves a pressure vessel roughing filter configuration where the pilot tubes 1211, 1212, 1213, 1214, 1215 of the same media, Media A are all connected in series within the pilot skid 1219. Also shown are two units 1226, 1227 for respective medias, Media B and Media C. The second unit 1226 comprises tubes 1231, 1232, 1233, 1234, 1235 housing filter Media B, and the third unit 1227, houses filter Media C in the tubes 1241, 1242, 1243, 1244, 1245. The arrangement depicted in FIG. 24 provides an example of apparatus and a method for pressure vessel roughing filter pilot implementation. FIG. 24 illustrates an example of a pilot method for a pressure vessel roughing filter configuration where the pilot tubes of the same media are connected in series within a pilot skid (e.g., providing three discrete testing units 1225, 1226, 1227 of the skid 1219). The view is shown from the top and shows how multiple media types can be tested in parallel with multiple trains of series connected pilot columns.

Figure 25:
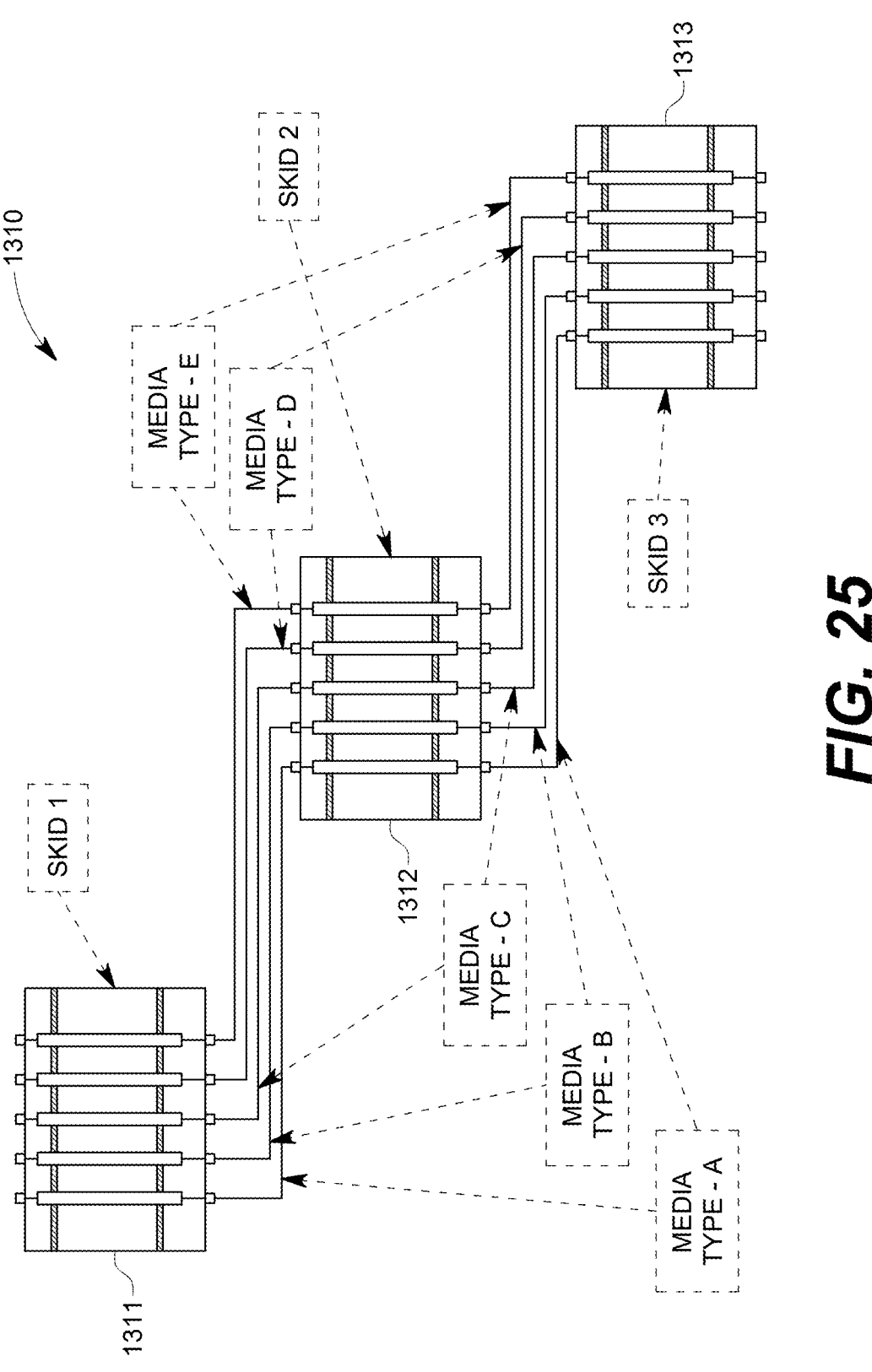
FIG. 25 is a schematic illustration showing a front elevation view of a pressure vessel roughing filter pilot example for multiple skids, according to an exemplary embodiment of the invention.

FIG. 25 shows an alternative pilot method for a pressure vessel roughing filter configuration and system 1310 according to the invention where multiple skids 1311, 1312, 1313 are connected in series. The output of a media column from one skid corresponds to the input of the column of another skid to create the series connection between columns. As illustrated, in the exemplary implementation and embodiment of FIG. 25, there are a plurality of media types, namely, Media Type A, Media Type B, Media Type C, Media Type D. and Media Type E. As shown the respective media types are arranged so the flow from the first skid of the same media type flows into the tube or tank of the second skid, having the same media type and from there into the tank of the third skid, having the same media type.

Figure 26:
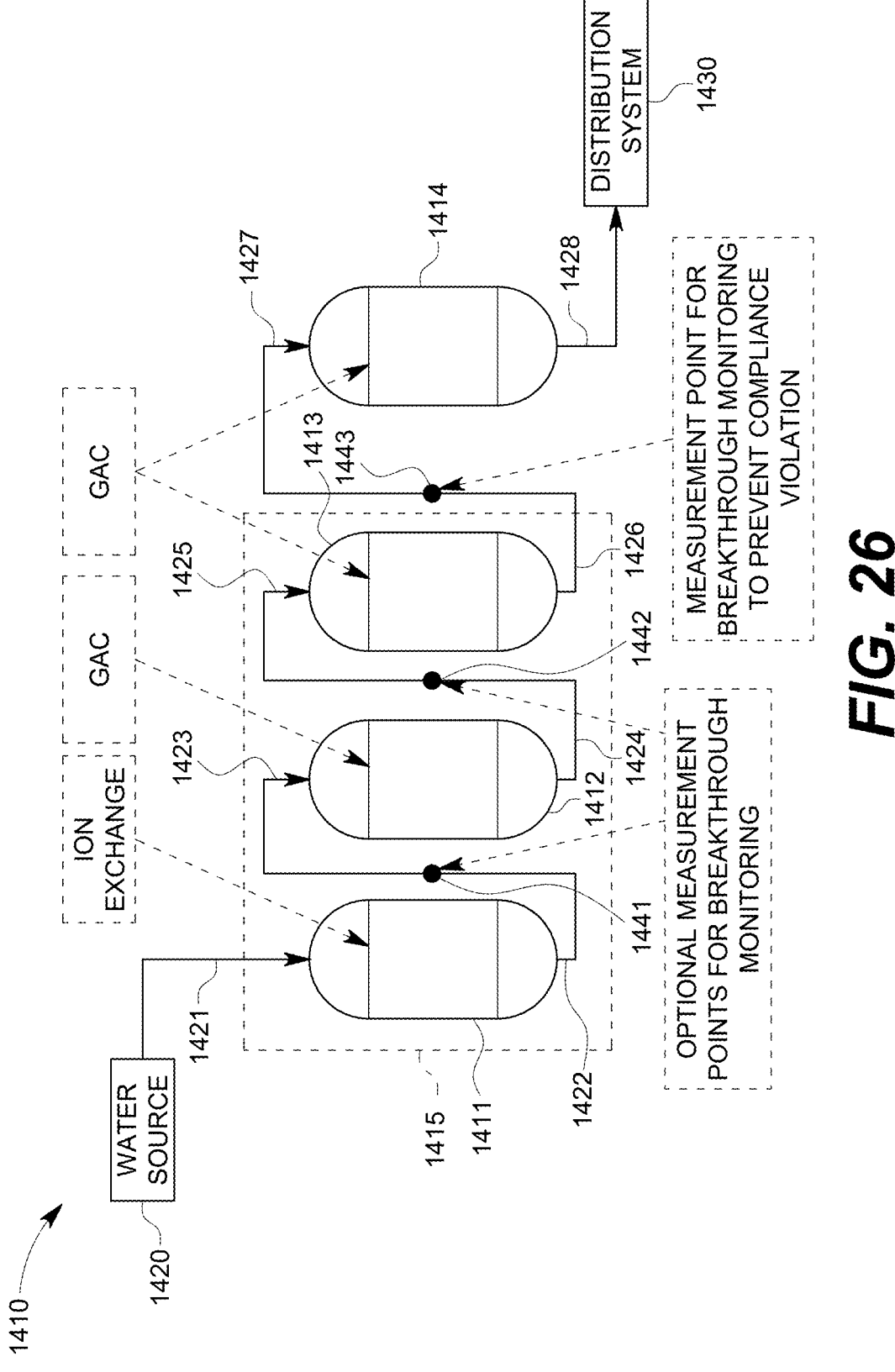
FIG. 26 is a schematic illustration showing a front elevation view of an exemplary configuration of a pressure vessel roughing filter system with different medias per vessel, according to an exemplary embodiment of the invention.

Referring to FIG. 26, there is illustrated a schematic illustration showing an exemplary implementation and apparatus according to the invention providing an example of using multiple media varieties within a single treatment train arrangement 1410 for pressure vessel roughing filter design at cither full scale or pilot scale. A plurality of tanks 1411, 1412, 1413, 1414 are shown. The first three tanks 1411, 1412, 1413 represent the roughing filter 1415. The roughing filter system 1410 in the exemplary embodiment shows a plurality of tanks comprising the roughing filter 1415, having a plurality of respective media types in a respective tank. Two of the pressure vessels 1412, 1413 are provided with media type that comprises granular activated carbon (GAC), while one of the pressure vessels 1411 of the roughing filter 1415 is shown comprising a different type of filter, such as an ion-exchange filter or anion exchange filter. The water source 1420 is shown entering the first pressure vessel 1411, at the inlet line 1421, while the outlet line 1422 of the first pressure vessel 1411 leads to the inlet 1423 of the second pressure vessel 1412, and the outlet line 1424 of the second pressure vessel 1412 leads to the inlet line 1425 of the third pressure vessel 1413, and the outlet 1426 of the third pressure vessel 1413 leads to the inlet 1427 of the final pressure vessel 1414. The outflow from the outlet 1428 from the final vessel 1414 is supplied for distribution 1430 to an intended source, for further processing and/or distribution to a water system. According to preferred embodiments a plurality of measurement points which may comprise sampling ports 1441, 1442, 1443 between the respective pressure vessels 1411, 1412, 1413, 1414 are shown. Sampling may be taken from the sampling ports. The sampling port 1443 between the final pressure vessel 1413 of the roughing system 1415 preferably is used to provide the samples for the breakthrough determination, such as for compliance adherence and monitoring.

Figure 27:
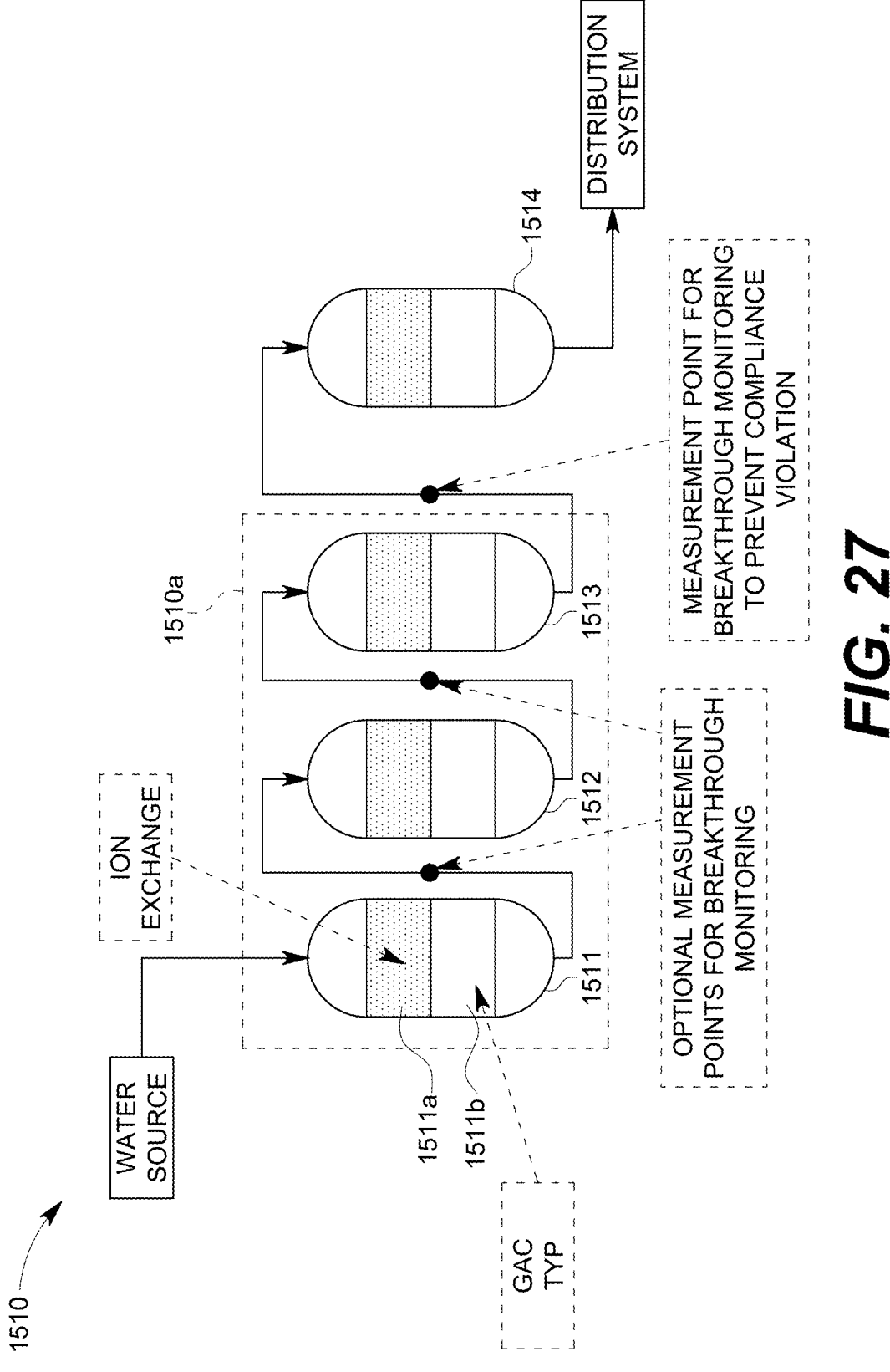
FIG. 27 is a schematic illustration showing a front elevation view of an exemplary configuration of a pressure vessel roughing filter system with different medias layers in a vessel, according to an exemplary embodiment of the invention.

FIG. 27 shows an example of using multiple media varieties within a single vessel for pressure vessel roughing filter design at either full scale or pilot scale. The system 1510 is shown according to an exemplary implementation and embodiment of the invention, with the pressure vessel roughing system 1510$a$ being shown comprising three pressure vessels 1511, 1512, 1513, connected in series with a final pressure vessel 1514. Referring to pressure vessel 1511, there is illustrated a representation of multiple and/or different media types within the pressure vessel 1511, which is shown provided in an arrangement of layers, comprising a first layer 1511$a$ of a first filter media type and a second layer 1511$b$ of a second filter media type. In the exemplary embodiment depicted, the first layer 1511$a$ comprises an ion exchange media, and the second layer 1511*b* comprises granular activated carbon (GAC).

The roughing filter apparatus and methods of the invention are designed to handle situations where the forecasted media usage encounters unanticipated changes in the source water or other conditions, which may be due to an event, or other activity affecting the water source or the filter system. Therefore, in certain conditions, the lead/lag filter rate may be reduced (where the adsorptive capacity of the filter media is reached earlier than the anticipated flow volume). In other conditions, the lead/lag filter rate may be extended (where there is potential for additional adsorption capacity of the filter media). The filter media has a design loading rate representing a capacity at which the filter may filter contaminants, such as for example PFAS contaminants. The roughing filter methods and devices disclosed herein may be used to determine utilization of a filter media to optimize the capacity while providing suitable filtration of contaminants, such as for example, PFAS contaminants.

In some cases, there are times when a traditional facility's lead/lag filter rate is reduced below the design loading rate, increasing the risk of premature PFAS breakthrough. For example, this may be due to effects such as channeling, because a surface water plant has seasonal cold water/flood chemistry issues or an intake problem. Because traditional lead/lag systems can be impacted by this type of seasonal flow reduction, loading rates can be insufficient to prevent premature breakthrough. The roughing filter methods and apparatus of the invention can be sized to prevent variable flow breakthroughs by extending EBCT across smaller vessels and by controlling flow to allow for proper diversion of adequate rates to vessels sized to have acceptable surface area loading rates under variable flow conditions.

In addition, there are times when a traditional facility's lead/lag filter rate is reduced below the design loading rate, increasing the risk of premature PFAS breakthrough due to channeling in other circumstances, such as for example, because a groundwater well has issues like poor pump performance or is obstructed by buildup of calcium and magnesium salts, iron and manganese compounds, or plugging caused by bio-fouling. Because traditional lead/lag systems can be impacted by variable well flow rates, loading rates can be insufficient to prevent premature PFAS breakthrough and the roughing filter methods and apparatus of the invention can be sized to prevent variable flow breakthroughs by extending EBCT across smaller vessels and by controlling flow to allow for proper diversion of adequate rates to vessels sized to have acceptable surface area loading rates under variable flow conditions Embodiments and implementations of the method and the apparatus and devices shown, according to some applications of use may be situated on a trailer for portability in transporting the system of pressure vessels, and/or sampling containers or apparatus to a water source being monitored. For example, the pressure vessels may be installed at a fixed location, or may be carried on a trailer at a desired location where filtration of a water source, evaluation of the filter media or where sample collection for a breakthrough test or forecast is carried out. One or more valves may direct water from the water source through the tubes, vessels, or other containment where the filter media is being evaluated. In addition, valves, flowmeters and pumps may be used to regulate and direct the flow of water such as the water source used for the breakthrough test or forecast through the system of filter media and sample containers. According to some embodiments, the roughing filters of the invention may be installed at a location where the main filters are situated, or alternatively, may be arranged on a trailer and brought to the location of the main filters, and connected thereto, allowing removal or swapping of the filters, when needed. For example, the connections via piping or other conduits may be manipulated through the use of valves, so that the roughing filter may switch water input from one vessel to another vessel, and vice versa, allowing the vessels to remain in place, but providing the flow through any one vessel prior to any one other vessel or vessels.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. Features disclosed in one embodiment may be implemented in one or more of the other embodiments, separately or in combination with other features. While the system, devices and methods of the invention have been disclosed in detail, and the preferred embodiments and best mode for practice of the invention have been similarly disclosed, the scope of exclusive rights to which the invention is entitled is defined by the claims appended hereto and by equivalents that perform substantially the same function in substantially the same way to achieve the same result.

What is claimed is:

1. A method for removal of contaminants from a water source or wastewater source, comprising:

a) flowing the water source or wastewater source through a filter system, the filter system comprising a contaminated water or wastewater inlet, a filtered water outlet, one or more vessels in communication with the contaminated water or wastewater inlet and the filtered water outlet, filter media contained in one or more vessels, wherein the filter media contained in the one or more vessels removes the one or more contaminants from the water source or wastewater source and maintains the concentration of the one or more contaminants at or lower than a designated concentration level for the one or more contaminants, for filtered water flowing from the filtered water outlet, b) wherein the one or more vessels have an inlet and an outlet, wherein at least one or more of the inlets of the one or more vessels comprises or is in communication with the contaminated water or wastewater inlet, and wherein at least one or more of the outlets of the one or more vessels comprises or is in communication with the filtered water outlet;

c) wherein the filter media is effective to remove the one or more contaminants from the water source or wastewater source, by flowing the water source or wastewater source through an inlet of the one or more vessels;

d) wherein the filter media is in fluid communication between the at least one contaminated water or waste water inlet and at least one filtered water outlet;

e) wherein flowing the water source or wastewater source through the filter system comprises flowing the water source or wastewater source at a flow rate to allow the flow of the water source or wastewater source that flows into the one or more vessels to have contact time with the filter media contained in the one or more vessels to remove the one or more contaminants;

f) wherein the effectiveness of the filter media that removes the one or more contaminants from the water source or wastewater source is an amount of filter media that effectively filters the one or more contaminants from the water source or wastewater source, and removes the one or more contaminants from the water source or wastewater source, for a flow total amount of volume of the water source or wastewater source containing the one or more contaminants that flows through the filter media contained in the one or more vessels, g) wherein the flow total volume of the water source or wastewater source containing the contaminants that the filter media removes contaminants from comprises the flow total volume that is a breakthrough volume;

h) wherein the breakthrough volume is generated by:

i) flowing water from the water source or wastewater source into pilot filter media, wherein the pilot filter media comprises the same media type as the filter media that is effective to remove the one or more contaminants from the water source or wastewater source;

ii) collecting a plurality of samples from the water source or wastewater source;

iii) wherein the plurality of samples from the water source or wastewater source include at least a plurality of samples from the water source or wastewater source after the water source or wastewater source has been in contact with the pilot filter media;

iv) wherein the plurality of samples from the water source taken after contact with the pilot filter media comprises a batch of samples;

v) generating for each respective sample of the batch of the plurality of samples collected from the water source or wastewater source that have been in contact with the pilot filter media a respective concentration of the one or more contaminants present in each of the respective samples of the batch;

vi) wherein generating the concentration of the one or more contaminants present in each of the respective plurality of the samples of the batch is carried out with a contaminant analyzer that generates the concentration of the one or more contaminants in each respective sample of the plurality of samples of the batch;

vii) wherein for each respective sample of the batch there is a concentration of the one or more contaminants that is greater than or equal to zero, and wherein for each respective sample of the batch there is a respective correspondent amount of the pilot filter media with which the water source or wastewater source from which each respective one of the plurality of samples of the batch has been in contact therewith, wherein the respective correspondent amount of the pilot filter media with which the water source or wastewater source from which each respective one of the plurality of samples of the batch has been in contact therewith provides a breakthrough forecasted filter media amount; and viii) wherein the amount of filter media in f) that effectively filters the one or more contaminants from the water source or wastewater source, and removes the one or more contaminants from the water source or wastewater source to maintain the concentration of the one or more contaminants at or lower than the designated concentration level for the one or more contaminants, for filtered water flowing from the filtered water outlet, for a flow total amount of volume of the water source or wastewater source containing the one or more contaminants that flows through the filter media contained in the one or more vessels, is the breakthrough forecasted filter media amount from the plurality of samples for the designated concentration level of the one or more contaminants.

2. The method of claim 1, wherein the breakthrough forecasted filter media amount from the plurality of samples for the designated concentration level of the one or more contaminants in viii) is measured in bed volumes, and the filter media amount is the forecasted bed volume of media that maintains the concentration of the one or more contaminants at or lower than the designated concentration level for the one or more contaminants, for filtered water flowing from the filtered water outlet.

3. The method of claim 1, wherein the breakthrough forecasted filter media amount from the plurality of samples for the designated concentration level of the one or more contaminants in viii) is measured in bed volumes, and the filter media amount is the forecasted depth of the filter media that maintains the concentration of the one or more contaminants at or lower than the designated concentration level for the one or more contaminants, for filtered water flowing from the filtered water outlet.

4. The method of claim 1, wherein the method comprises an electronically actuated method, and further comprises actuating a controller to provide the breakthrough forecast, and the breakthrough forecasted filter media amount for the filter media from the concentration of contaminants for each respective sample of the batch and the respective pilot filter media volume for each sample of the batch, wherein the breakthrough forecasted filter media amount for the filter media comprises the filter media amount in the vessels of the filter system.

5. The method of claim 4, wherein the filter media amount in the filter system is distributed among the one or more vessels in communication with the contaminated water or wastewater inlet and the filtered water outlet.

6. The method of claim 1, wherein generating the breakthrough volume in step h) comprises providing one or more pilot vessels, and wherein the pilot filter media is contained in the one or more pilot vessels.

7. The method of claim 6, wherein at least some of the one or more pilot vessels contain different amounts of pilot filter media.

8. The method of claim 6, wherein each of the one or more pilot vessels contains a different amount of the pilot filter media.

9. The method of claim 1, wherein the filter media contained in the one or more vessels is provided in a media space within each of the one or more vessels.

10. The method of claim 6, wherein the breakthrough forecasted filter media amount, is an amount of filter media from a forecasted volume of filter media from the concentration of the one or more contaminants of each respective sample of the batch versus the pilot filter media amount contained in each respective ones of the pilot vessels.

11. The method of claim 1, wherein the forecasted breakthrough volume is generated without an actual breakthrough of the pilot filter media.

12. The method of claim 1, wherein the filter media is a single filter media type.

13. The method of claim 1, wherein the filter media is a plurality of filter media types, and wherein the breakthrough volume of filter media is generated by carrying out steps h) i) through viii) for each media type of the plurality of filter media types.

14. The method of claim 1, wherein collecting the samples is carried out by actuating a valve provided for each sample location on each one of the respective plurality of vessels.

15. The method of claim 1, wherein collecting the plurality of samples from the water source or wastewater source samples in step h) ii) is carried out manually by opening a flow control valve to admit flow from a sample port of the vessel into a sample vial.

16. The method of claim 1, wherein collecting the plurality of samples from the water source or wastewater source samples in step h) ii) is carried out via automated flow control valves actuated based on the timer or an operator signal, to open a respective plurality of flow control valves to admit flow from respective sample ports of the respective vessels into a respective sample vial, wherein each automated flow control valve is associated with a respective one of the sample ports of each vessel.

17. The method of claim 1, wherein collecting the samples is carried out manually by opening a valve to allow flow from a sample port of the vessel into a sample vial.

18. The method of claim 1, wherein the filter media comprises granular activated charcoal (GAC).

19. The method of claim 1, wherein the filter media comprises ion exchange filter media.

20. The method of claim 1, wherein the filter media comprises a mixed filter media, including a first type of filter media, and a second type of filter media.

21. The method of claim 20, wherein at least one of the first type of filter media and the second type of filter media comprises granular activated charcoal (GAC).

22. The method of claim 20, wherein at least one of the first type of filter media and the second type of filter media comprises ion exchange filter media.

23. The method of claim 20, wherein the first type of filter media comprises granular activated charcoal (GAC), and wherein the second type of filter media comprises ion exchange filter media.

* * * * *